US009220607B2

(12) United States Patent
Palmatier et al.

(10) Patent No.: US 9,220,607 B2
(45) Date of Patent: Dec. 29, 2015

(54) PIVOTABLE INTERBODY IMPLANT SYSTEM

(75) Inventors: Stanley T. Palmatier, Olive Branch, MS (US); Keith M. Miller, Germantown, TN (US); Charles L. Branch, Advance, NC (US); William D. Armstrong, Memphis, TN (US); Anthony J. Melkent, Memphis, TN (US); Thomas Drochner, Memphis, TN (US); Richard A. Hynes, Melbourne Beach, FL (US); Jonathan Blackwell, Arlington, TN (US); Kidong Yu, Memphis, TN (US)

(73) Assignee: Warsaw Oorthopedic, Inc., Warsaw, IN (US)

( * ) Notice: Subject to any disclaimer, the term of this patent is extended or adjusted under 35 U.S.C. 154(b) by 934 days.

(21) Appl. No.: 13/283,915

(22) Filed: Oct. 28, 2011

(65) Prior Publication Data

US 2013/0110241 A1 May 2, 2013

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC .............. *A61F 2/4465* (2013.01); *A61F 2/447* (2013.01); *A61F 2/4611* (2013.01); *A61F 2002/2817* (2013.01); *A61F 2002/2835* (2013.01); *A61F 2002/3008* (2013.01); *A61F 2002/3083* (2013.01); *A61F 2002/30092* (2013.01); *A61F 2002/30523* (2013.01); *A61F 2002/30538* (2013.01); *A61F 2002/30677* (2013.01); *A61F 2002/30777* (2013.01); *A61F 2002/30784* (2013.01); *A61F 2002/30827* (2013.01); *A61F 2002/30828* (2013.01); *A61F 2002/4475* (2013.01); *A61F 2310/00017* (2013.01); *A61F 2310/00023* (2013.01); *A61F 2310/00029* (2013.01); *A61F 2310/0097* (2013.01); *A61F 2310/00221* (2013.01); *A61F 2310/00293* (2013.01); *A61F 2310/00359* (2013.01)

(58) Field of Classification Search
CPC ....... A61F 2/442; A61F 2/4611; A61F 2/447; A61F 2/4465; A61F 2/44; A61F 2002/4475; A61F 2002/2835; A61F 2002/30904; A61F 2002/30841; A61F 2002/30828
USPC ............................................ 623/17.16, 17.11
See application file for complete search history.

(56) References Cited

U.S. PATENT DOCUMENTS

| 5,306,309 | A | * | 4/1994 | Wagner et al. | ............. 623/17.16 |
| 6,685,742 | B1 | | 2/2004 | Jackson | |
| 7,497,859 | B2 | | 3/2009 | Zucherman et al. | |
| 7,691,146 | B2 | | 4/2010 | Zucherman et al. | |
| 7,824,411 | B2 | | 11/2010 | Varieur et al. | |
| 7,824,413 | B2 | | 11/2010 | Varieur et al. | |
| 7,850,736 | B2 | | 12/2010 | Heinz | |
| 7,862,618 | B2 | | 1/2011 | White et al. | |

(Continued)

*Primary Examiner* — Jerry Cumberledge
*Assistant Examiner* — Tessa Matthews

(57) ABSTRACT

An interbody implant system is provided. The interbody implant system includes an implant having an engagement surface and an instrument including a first member and a second member that is movable relative to the first member. The first member is configured to capture the implant and the second member includes an interface configured to engage the engagement surface to releasably lock the implant in at least one orientation relative to the second member. The at least one of the engagement surface and the interface include at least one planar face. Methods of use are disclosed.

21 Claims, 27 Drawing Sheets

(56) References Cited

U.S. PATENT DOCUMENTS

| | | |
|---|---|---|
| 7,887,569 B2 | 2/2011 | Frigg |
| 7,901,458 B2 | 3/2011 | DeRidder et al. |
| 7,922,724 B2 | 4/2011 | Lim |
| 7,922,729 B2 | 4/2011 | Michelson |
| 7,927,334 B2 | 4/2011 | Miller et al. |
| 7,935,148 B2 | 5/2011 | Edie et al. |
| 7,959,675 B2 | 6/2011 | Gately |
| 7,967,863 B2 | 6/2011 | Frey et al. |
| 7,988,695 B2 * | 8/2011 | Dye ................... 606/86 A |
| 8,157,845 B2 * | 4/2012 | Warnick et al. ........... 606/279 |
| 8,858,637 B2 * | 10/2014 | Milz et al. ............. 623/17.16 |
| 2002/0055781 A1 | 5/2002 | Sazy |
| 2004/0153065 A1* | 8/2004 | Lim ............................ 606/53 |
| 2005/0096745 A1 | 5/2005 | Andre et al. |
| 2006/0235426 A1 | 10/2006 | Lim et al. |
| 2007/0162128 A1* | 7/2007 | DeRidder et al. ......... 623/17.11 |
| 2008/0009880 A1* | 1/2008 | Warnick et al. ............... 606/99 |
| 2008/0027544 A1 | 1/2008 | Melkent |
| 2008/0097454 A1 | 4/2008 | DeRidder et al. |
| 2008/0109005 A1 | 5/2008 | Trudeau et al. |
| 2008/0262623 A1* | 10/2008 | Bagga et al. ............. 623/17.16 |
| 2009/0234364 A1* | 9/2009 | Crook ............................ 606/99 |
| 2009/0276049 A1 | 11/2009 | Weiland |
| 2010/0094422 A1 | 4/2010 | Hansell et al. |
| 2010/0256760 A1* | 10/2010 | Hansell ................... 623/17.11 |
| 2011/0106259 A1* | 5/2011 | Lindenmann et al. ..... 623/17.16 |
| 2012/0010715 A1* | 1/2012 | Spann ..................... 623/17.16 |
| 2012/0029641 A1* | 2/2012 | Curran et al. ............. 623/17.16 |
| 2012/0165943 A1* | 6/2012 | Mangione et al. ......... 623/17.16 |
| 2013/0006362 A1* | 1/2013 | Biedermann et al. ...... 623/17.16 |
| 2013/0023937 A1* | 1/2013 | Biedermann et al. .......... 606/279 |
| 2014/0012385 A1* | 1/2014 | Baynham .................. 623/17.16 |
| 2014/0172105 A1* | 6/2014 | Frasier et al. ............. 623/17.16 |

* cited by examiner

PIVOTABLE INTERBODY IMPLANT SYSTEM

TECHNICAL FIELD

The present disclosure generally relates to medical devices, systems and methods for the treatment of musculoskeletal disorders, and more particularly to an interbody implant system and method that facilitates implant positioning for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions are caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY OF THE INVENTION

Accordingly, an interbody implant system and method is provided that facilitates implant positioning for treating a vertebral column. It is further contemplated that the implant system and method may be employed for an arthrodesis treatment using minimally invasive and percutaneous techniques.

In one embodiment, an interbody implant system is provided. The interbody implant system includes an implant having an engagement surface and an instrument including a first member and a second member that is movable relative to the first member. The first member is configured to capture the implant and the second member includes an interface configured to engage the engagement surface to releasably lock the implant in at least one orientation relative to the second member. The at least one of the engagement surface and the interface include at least one planar face.

In one embodiment, the interbody implant system includes an implant having a first end and a second end having an engagement surface including at least one planar face and a catch. An instrument extends between a first end and a second end. The instrument is movable relative to the first member. The first member includes a proximal end and a distal end. The distal end includes a capture surface configured to engage the catch. The capture surface is movable between an open position to release the catch and a closed position to capture the catch such that the implant is movable to a plurality of orientations. The second member includes a proximal end and a distal end. The distal end includes a planar interface configured to engage the at least one planar face of the engagement surface to releasably fix the implant relative to the distal end of the second member in one of the plurality of orientations between a first configuration such that the distal end of the second member is movable relative to the implant and a closed position to capture the catch such that the implant is movable to the second member to a plurality of orientations.

In one embodiment, the interbody implant system includes an implant including an engagement surface having a smooth arcuate configuration that defines a first radius of curvature. The system also includes an instrument having a first member and a second member that is movable relative to the first member. The first member is configured to capture the implant and the second member includes an interface having a smooth, arcuate configuration that defines a second radius of curvature. The second radius of the curvature is less than the first radius of curvature such that the interface engages the engagement surface in an interference fit to releasably lock the implant in at least one orientation relative to the second member.

In yet another embodiment, an interbody implant is provided having a body defining a longitudinal axis extending between a proximal end and a distal end. The proximal end including an inner surface having opposing transverse surfaces and defining an inner cavity having a proximal facing opening configured to receive an instrument. The proximal end further including a catch configured for disposal within the inner cavity and disposed in an orientation transverse to said longitudinal axis so that the catch is configured to be captured by the instrument. The proximal end of the interbody implant may also include opposing lateral faces that are disposed at an angular orientation relative to a longitudinal axis of the implant. The proximal end of the implant may also have at least one planar face that includes a proximal face disposed in a perpendicular orientation relative to a longitudinal axis of the implant, and a first lateral face that converges with the proximal face to form a first angle. The interbody implant may also have a second lateral face that converges with the proximal face to form a second angle, so that the implant is pivotable relative to the instrument via engagement of the instrument with at least one of said first and second angles.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
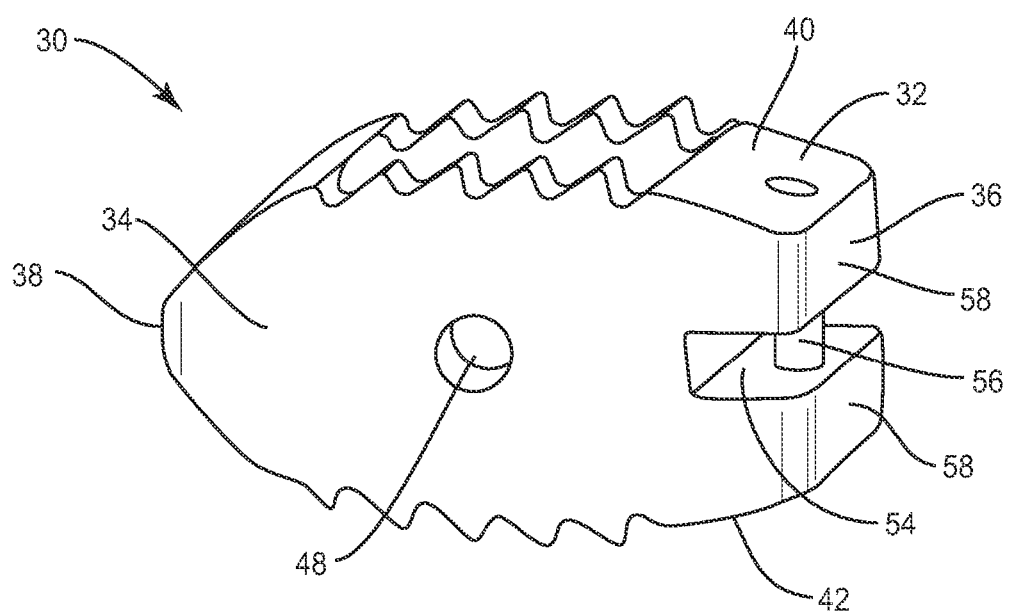
FIG. 1 is a perspective view of an implant of a system in accordance with the principles of the present disclosure.

The exemplary embodiments of the interbody implant system and related methods of use disclosed are discussed in terms of medical devices for the treatment of musculoskeletal disorders and more particularly, in terms of an interbody implant system that facilitates implant positioning for treating a vertebral column. It is envisioned that the interbody implant system, in general, may be employed for fusion and fixation treatments to provide decompression and/or restoration of lordosis. It is further envisioned that the interbody implant system and methods of use disclosed can be employed to obtain fusion of vertebrae through a minimally invasive or percutaneous technique. It is contemplated that the interbody implant is removable and/or may be repositioned. In one embodiment, the disclosed interbody implant system and methods of use can provide for manipulation of an interbody implant, which includes pivoting of the implant in an intervertebral space. In one embodiment, the system allows a practitioner to control the amount of pivot and relocate the implant after the implant is pivoted to a particular orientation.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed interbody implant system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The interbody implant system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the interbody implant system can be fabricated from biologically acceptable materials suitable for medical applications, including metals, synthetic polymers, ceramics and bone material and/or their composites, depending on the particular application and/or preference of a medical practitioner. For example, the components of the interbody implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the interbody implant system may have material composites, including the above materials, to achieve various desired characteristics such as strength, rigidity, elasticity, compliance, biomechanical performance, durability and radiolucency or imaging preference. The components of the interbody implant system, individually or collectively, may also be fabricated from a heterogeneous material such as a combination of two or more of the above-described materials.

The following discussion includes a description of an interbody implant system and related methods of employing the interbody implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-29, illustrated are components of an interbody implant system in accordance with the principles of the present disclosure.

Figure 2:
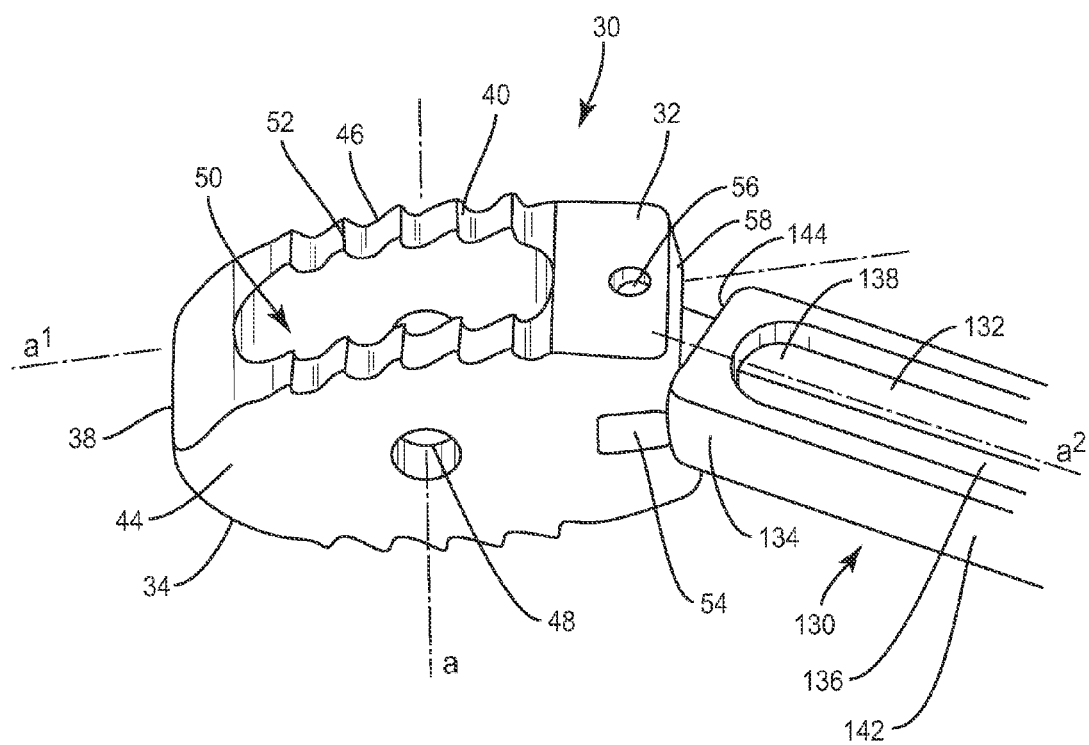
FIG. 2 is a perspective view of the implant shown in FIG. 1 and a break away view of an instrument of the system.

As shown in FIGS. 1-2, the interbody implant system includes a spinal implant 30 employed as a stabilization device in fusion and fixation procedures, for example, for patients suffering from a spinal disorder to provide height restoration between vertebral bodies, decompression and/or restoration of lordosis. The components of the interbody implant system may be monolithically formed, integrally connected or include fastening elements and/or instruments, for example, as described herein. Implant 30 is configured to be inserted between adjacent vertebrae and includes a first end, such as proximal end 32, and a second end, such as distal end 34, opposite proximal end 32, upper and lower surfaces 40, 42, and side surfaces 44, 46. Implant 30 has a height defined by the distance between upper and lower surfaces 40, 42 which is approximately the distance between two adjacent vertebrae and a width defined by the distance between proximal end 32 and distal end 34. The width of implant 30 is approximately the width of at least one of the vertebrae implant 30 is positioned between.

Proximal end 32 includes a proximal face 36, while distal end 34 includes a distal face 38. Upper and lower surfaces 40, 42 are configured to interface with load bearing endplates of adjacent vertebrae, while side surfaces 44, 46, proximal end 32 and distal end 34 extend between upper and lower surfaces 40, 42. In one embodiment, proximal face 36 is planar while distal face 38 is convexly curved between upper and lower surfaces 40, 42 and is configured to allow at least a portion of distal face 38 to be inserted into a collapsed, undistracted disc space. However, it is envisioned that distal face 38 may also be pointed, planar or concavely curved between upper and lower surfaces 40, 42.

Proximal end 32 includes at least one recess 54 disposed in a parallel orientation relative to transverse axis a. Recess 54 is sized and configured to receive at least a portion of an insertion instrument, such as instrument 130. In addition to or alternatively to recess 54, any other suitable structure or configuration for engagement by an insertion tool is contemplated, including one or more grooves, slots and/or holes in proximal end 32 that are threaded or unthreaded. In one embodiment, recess 54 is rectangular, however it is envisioned that recess 54 may have a polygonal shape including triangular, square, pentagonal, hexagonal, or may have a round or oval shape.

Recess 54 extends through side surfaces 44, 46. However, it is envisioned that recess 54 may be disposed within proximal end 32 of implant 30 without extending through side surfaces 44, 46, such that recess 54 is disposed between side surfaces 44, 46. Alternatively, recess 54 may be disposed within proximal end 32 of implant 30 while extending through only side surface 44 or side surface 46 and terminating between side surfaces 44, 46. Recess 54 is disposed equidistant between upper and lower surfaces 40, 42, however, it is envisioned that recess 54 may be disposed in proximal face 36 such that the top of recess 54 is closer to upper surface 40 than the bottom of recess 54 is from lower surface 42, or vice versa. Recess 54 has a depth extending longitudinally along longitudinal axis $a^1$ of implant 30 from proximal face 36 toward distal face 38 and terminates before distal face 38.

Recess 54 may include a catch 56, such as a cylindrical pin, which is configured to be captured by an instrument that facilitates positioning of spinal implant 30, such as instrument 130. In one embodiment, catch 56 is disposed through upper and lower surfaces 40, 42 in proximal end 32 of implant 30. However, it is envisioned that catch 56 may also be disposed in proximal end 32 of implant 30 without extending through upper and lower surfaces 40, 42. Alternatively, catch 56 may extend through upper surface 40 without extending through lower surface 42, or catch 56 may extend through lower surface 42 without extending through upper surface 40. In one embodiment, catch 56 is disposed in implant 30 in a perpendicular orientation relative to longitudinal axis $a^1$ of implant 30 such that implant 30 can be pivoted about catch 56 in an axial plane. Catch 56 is disposed a distance from proximal end 32 sufficient to allow an instrument, such as instrument 130, to engage catch 56 of implant 30 and pivot implant 30 axially about catch 56. Catch 56 is disposed equidistant between side surfaces 44, 46 such that catch 56 is the same distance from side surface 44 as side surface 46. It is also envisioned that catch 56 may be positioned such that the catch is closer to side surface 44 than side surface 46, or vice versa. Catch 56 is fabricated of a rigid material(s) such as stainless steel alloys, commercially pure titanium, titanium alloys, Grade 5 titanium, super-elastic titanium alloys, cobalt-chrome alloys, stainless steel alloys, man-made materials and combinations thereof that can withstand the torque associated with maneuvering implant 30.

Implant 30 further includes at least one engagement surface 58 configured to engage the engaging portion of an insertion instrument, such as instrument 130, to lock the rotation of implant 30 within instrument 130. That is, once the instrument engages catch 56, engagement surface 58 contacts the engaging portion of the instrument so as to prevent further pivoting of implant 30 about catch 56. In one embodiment, engagement surface 58 includes at least a portion of proximal face 36 above and below recess 54. Engagement surface 58 is planar and is disposed in a parallel orientation relative to transverse axis a of spinal implant 30. Alternatively, as described further below, engagement surface 58 can be angled relative to transverse axis a. The size and shape of engagement surface 58 corresponds to the size and shape of the corresponding portion of instrument 130 that engages engagement surface 58, further details of which will be provided below.

In one embodiment, side surfaces 44, 46 are parallel to one another and are both planar. However, it is envisioned that side surfaces 44, 46 may also be convexly curved between upper and lower surfaces 40, 42 and/or proximal end 32 and distal end 34 such that at least a portion of side surfaces 44, 46 have a rounded portion to facilitate insertion of implant 30 into a collapsed, undistracted disc at a variety of angles, leading with the rounded portion of side surfaces 44, 46.

Upper and lower surfaces 40, 42, side surfaces 44, 46, proximal end 32 and distal end 34 include at least one aperture 48 that may receive anchor members for attachment of implant 30 to vertebrae, engage a surgical instrument and/or receive a bone graft. In one embodiment, aperture 48 is a cylindrical bore extending through side surfaces 44, 46 and is disposed in a parallel orientation relative to a transverse axis a of implant 30. Aperture 48 may assume a variety of shapes depending upon the function of aperture 48. For example, if aperture 48 is used to receive bone graft, aperture 48 may have a size and shape corresponding to the size and shape of the bone graft and/or an instrument used to insert the bone graft within aperture 48. Aperture 48 may be oval, triangular, polygonal, square or rectangular, for example.

A hollow center 50 opening at upper and lower surfaces 40, 42 allows for placement of materials, such as bone growth materials, to promote bonding and/or fusion of implant 30 to adjacent vertebrae. In one embodiment, hollow center 50 has an oval shape and is disposed along the longitudinal axis $a^1$ of implant 30. It is also envisioned that hollow center 50 may be disposed through side surfaces 44, 46 and may assume a variety of shapes depending upon, for example, the shape of the vertebrae implant 30 is inserted between and/or the type of material placed therein. That is, hollow center 50 may have a shape that corresponds to the shape of the vertebrae implant 30 is inserted between. Hollow center 50 may be in communication with aperture 48.

Upper and lower surfaces 40, 42 of implant 30 include bone engaging features 52 configured to reduce slipping or movement relative to the vertebrae implant 30 is placed between. In one embodiment, bone engaging features 52 are on the entire area of upper and lower surfaces 40, 42, but can also be provided on a portion of these surfaces. In one embodiment, bone engaging features 52 are angled teeth that permit introduction into the disc space, but also restrict removal. It is contemplated that bone engaging features 52 may include other features such as protrusions or keels, which may or may not restrict removal of implant 30. It is further contemplated that the upper and lower surfaces 40, 42 of implant 30 may be free of bone engaging features 52, such that the upper and lower surfaces 40, 42 of implant 30 are relatively smooth. In one embodiment, upper surface 40 includes bone engaging features 52 to engage an adjacent vertebra, while lower surface 42 is smooth to permit another of the adjacent vertebra to be moved along and in contact with the smooth surface of lower surface 42 as corrective forces are applied to manipulate the other of the adjacent vertebrae into alignment.

In addition to implant 30, as mentioned above, the system of the present invention also includes instrument 130. Instrument 130 is configured to engage implant 30, pivot implant 30 relative to instrument 30, lock implant 30 at a particular angle relative to instrument 130 and insert implant 30 at the desired angle. Instrument 130 includes a first member 132 and a second member 134 that is movable relative to first member 132. Second member 134 is a sleeve configured to fit about first member 132 and has an opening in a distal end 144. It is envisioned that first member 132 and/or second member 134 and may be rectangular, cylindrical or, in the alternative, and may have other cross section shapes such as square, hexagonal or octagonal, for example.

Figure 3:
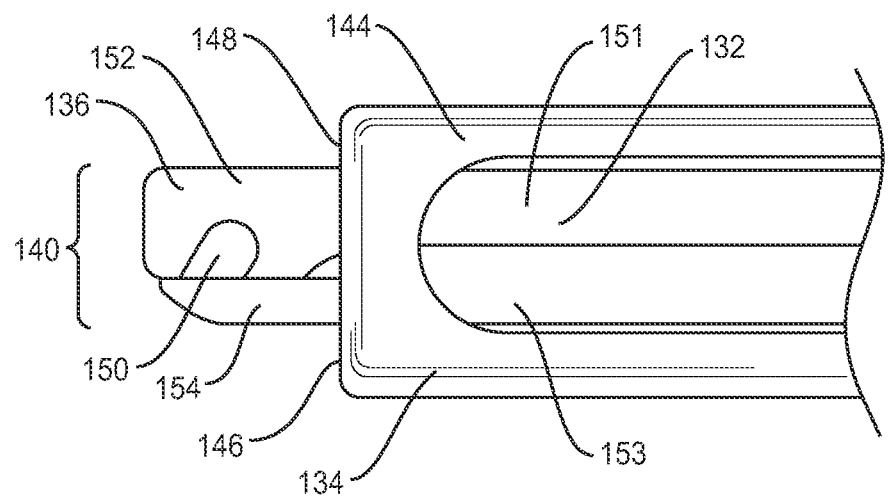
FIG. 3 is a top, break away view of the instrument shown in FIG. 2.

First member 132 includes a proximal end 136 and a distal end 138 having a capture surface 140, shown in FIG. 3, configured to engage catch 56 of implant 30. Capture surface 140 is offset from the bottom of recess 54 so as to prevent friction between implant 30 and instrument 130. Distal end 138 of first member 132 is bifurcated longitudinally into a top portion 151 and a bottom portion 153, bottom portion 153 is moveable relative to top portion 151. The distal end of top portion 151 forms a hook 152 having a cavity 150, while the distal end of bottom portion 153 forms a gate 154 which translates relative to hook 152 to cover at least a portion of cavity 150. Hook 152 and gate 154 each have a length which is less than the depth of recess 54 such that when capture surface 140 is inserted into recess 54, capture surface 140 may engage catch 56 and pivot about catch 56 without contacting the sides of recess 54, thus allowing instrument 130 to freely pivot about catch 56. Cavity 150 has a size and shape that corresponds to that of catch 56, such that implant 30 will be permitted to pivot about catch 56 when engaged with instrument 130. In one embodiment, cavity 150 includes top and right portions that are curved, a left portion that is angled and a bottom portion that is planar. This configuration facilitates capture of a cylindrical pin, such as catch 56, while providing space for catch 56 to pivot within cavity 150. Catch 56 may be positioned within cavity 150 when capture surface 140 is in an open position. Gate 154 then translates relative to hook 152 to capture catch 56 within cavity 150, thus moving capture surface 140 to a closed position.

Second member 134 includes a proximal end 142 and a distal end 144 having an interface 146 configured to engage engagement surface 58 to releasably lock implant 30 in at least one orientation relative to second member 134. Interface 146 and engagement surface 58 each include at least one planar face such that interface 146 could be positioned perpendicarly against engagement surface 58, when capture surface 140 engages catch 56, to lock implant 30 at an angle relative to instrument 130 by preventing implant 30 from pivoting about catch 56. In one embodiment, interface 146 includes a distal face 148 of distal end 144, wherein distal face 148 is disposed in a perpendicular orientation relative to a longitudinal axis $a^2$ of instrument 130. It is envisioned that distal face 148 may be disposed at multiple angles ranging from 0 to 90° and from 0 to −90° relative to a longitudinal axis $a^2$ of instrument 130. To lock implant 30 in a particular orientation relative to second member 134, interface 146 of second member 134 is advanced toward proximal face 36 of implant 30 until interface 146 engages proximal face 36, thereby preventing implant 30 from pivoting or rotating about catch 56.

Instrument 130 may include a handle having a transverse dimension greater than that of second member 134 to permit ease of gripping by a surgeon during use. The handle may be formed of stainless steel, for example, and may have a shape corresponding to that of second member 134. For example, it is envisioned that the handle could be cylindrical or, in the alternative, may have other cross section shapes such as square or rectangle, for example. The handle may also have flattened surfaces for receiving hammer blows used to manipulate instrument 130 to pivot and/or position an implant 30 into the intervertebral disc space.

Figure 4:
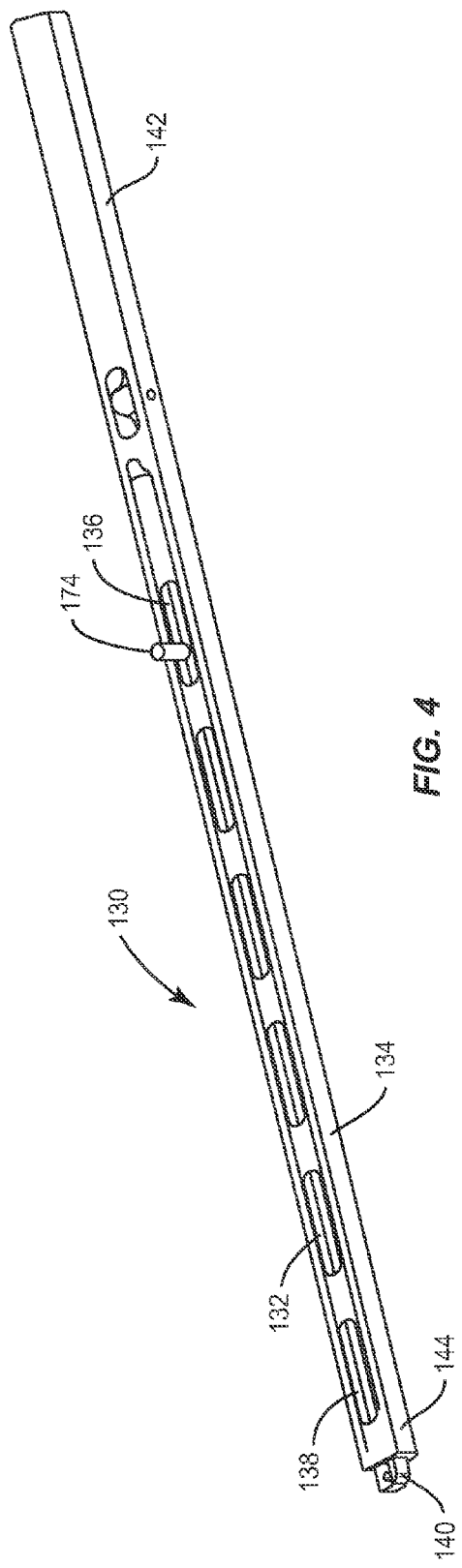
FIG. 4 is a perspective view of the instrument shown in FIG. 2.
Figure 5:
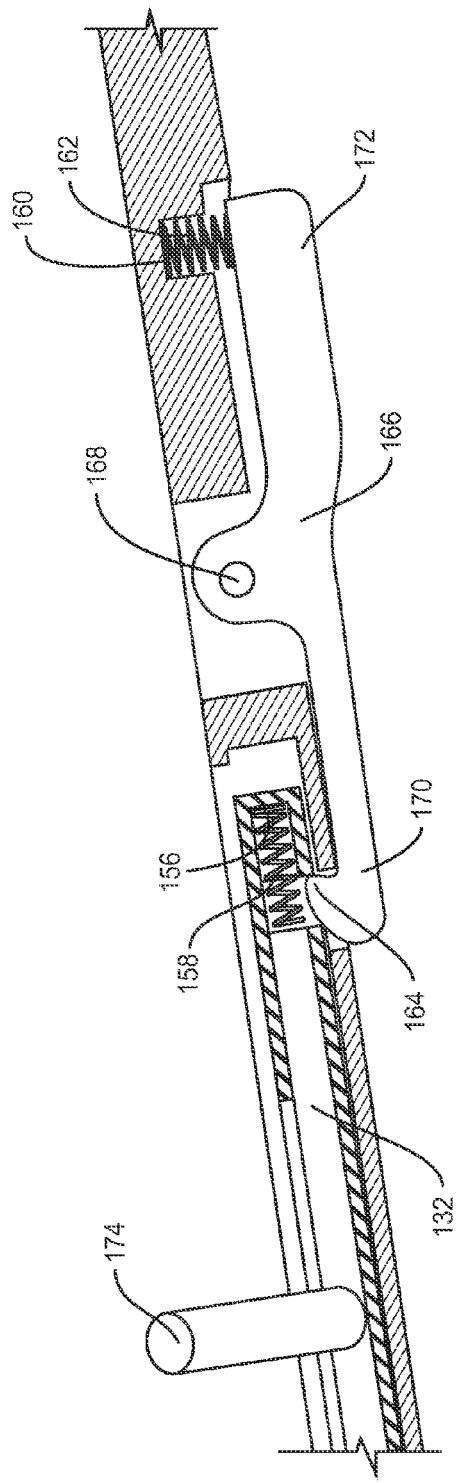
FIG. 5 is an enlarged side, cutaway view of the instrument shown in FIG. 4.

As shown in FIGS. 4 and 5, capture surface 140 may be translated from an open position to a closed position via a spring mechanism. Capture surface 140 includes a hook and gate mechanism, as shown in FIG. 3. Second member 134 includes at least one first recess 156 disposed within second member 134 in a parallel orientation relative to longitudinal axis $a^2$ of instrument 130. First recess 156 includes a first spring 158 inserted therein and disposed in a parallel orientation relative to longitudinal axis $a^2$ of instrument 130. Second member 134 further includes a second recess 160 disposed in a perpendicular orientation relative to longitudinal axis $a^2$ of instrument 130 extending from the center portion of second member 134 through a bottom surface of second member 134. Second recess 160 includes a second spring 162 inserted therein and disposed in a perpendicular orientation relative to longitudinal axis $a^2$ of instrument 130. Second member 134 also includes a notch 164 disposed in a perpendicular orientation relative to longitudinal axis $a^2$ of instrument 130 extending from the center portion of second member 134 through a bottom surface of second member 134. Notch 164 is proximal to first recess 156 and first spring 158. An arm 166 extends between first recess 156 and notch 164. At least a portion of a distal end 170 of arm 166 is configured to fit within notch 164 such that distal end 170 covers at least a portion of notch 164, and at least a portion of the proximal end 172 of arm 166 is configured to fit within second recess 160 such that proximal end 172 covers at least a portion of second recess 160. Arm 166 includes a pivot point 168 positioned between notch 164 and second recess 160. Pivot point 168 is disposed through second member 134 such that pivoting arm 166 about pivot point 168 allows distal end 170 of arm 166 to be removed from notch 156 with proximal end 172 inserted into second recess 160 or proximal end 172 of arm 166 to be removed from second recess 160 with distal end 170 inserted into notch 164. Distal end 170 contacts at least a portion of second spring 162 to maintain second spring 162 in its compressed configuration. When second spring 162 is decompressed, distal end 170 moves perpendicularly relative to longitudinal axis $a^2$ of instrument 130 such that distal end 170 moves away from a bottom portion of second member 134. Proximal end 172 of arm 166 is inserted into at least a portion of notch 164 and contacts at least a portion of first spring 158 within first recess 156 to maintain first spring 158 in its compressed configuration. Pivoting arm 166 about pivot point 168 toward distal end 170 of arm 166 causes second spring 162 to compress, which in turn causes proximal end 172 of arm 166 to be removed from notch 164 as first spring 158 decompresses. Decompressing first spring 158 allows bottom portion 153 of first member 132 with gate 154 fixed to the distal end thereof to move distally, translating gate 154 over at least a portion of cavity 150 within hook 152 and capturing catch 56 within cavity 150. To move capture surface 140 to an open position, a handle 174 may be moved toward a proximal end of instrument 130 causing first spring 158 to compress. As first spring 158 is compressed, arm 166 is pivoted about pivot point 168 toward proximal end 172, causing second spring 162 to decompress, which in turn inserts proximal end 172 of arm 166 into second recess 164. Distal end 144 of second member 134 may be advance to engage engagement surface 58 of implant 30 using a thread mechanism, a ratcheting mechanism, or a latch mechanism.

Figure 6:
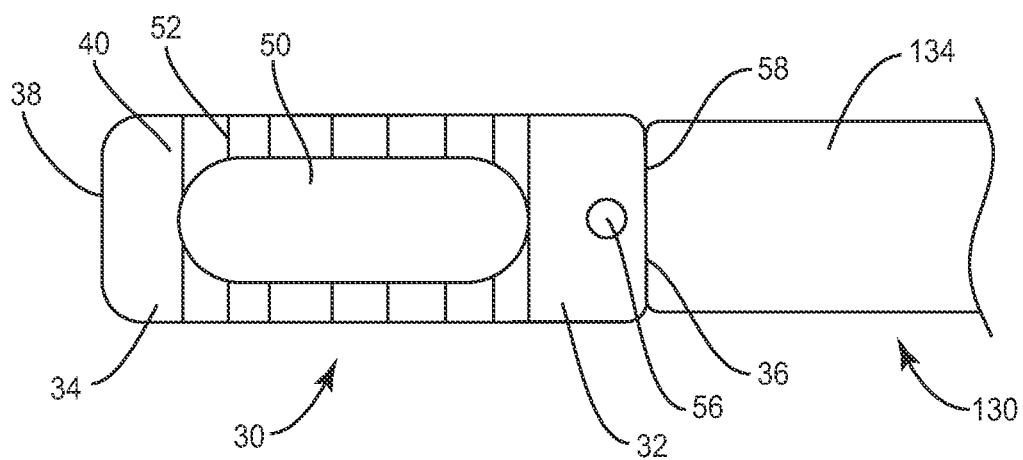
FIG. 6 is a top, break away view of the implant and the instrument shown in FIG. 2.

Implant 30 may be locked to instrument 130 in a straight orientation where it is desirable to insert implant 30 between two adjacent vertebrae leading with distal face 38 of implant 30. As shown in FIG. 6, engagement surface 58 is proximal face 36 of implant 30 and is planar, as is interface 146. To insert implant 30 into an intervertebral space with implant 30 locked to instrument 130 in a straight orientation, capture surface 140 is inserted into recess 54 of implant 30 in an open position and is positioned to engage catch 56 within cavity 150. Capture surface 140 is then moved to a closed position, which captures catch 56 within cavity 150. To lock implant 30 in a straight orientation, interface 146 of second member 134 is advanced toward proximal face 36 of implant 30 until interface 146 engages proximal face 36, thereby preventing implant 30 from pivoting about catch 56. Implant 30 may then be inserted into an intervertebral space in a straight orientation, leading with distal face 38 of implant 30.

Figure 7:
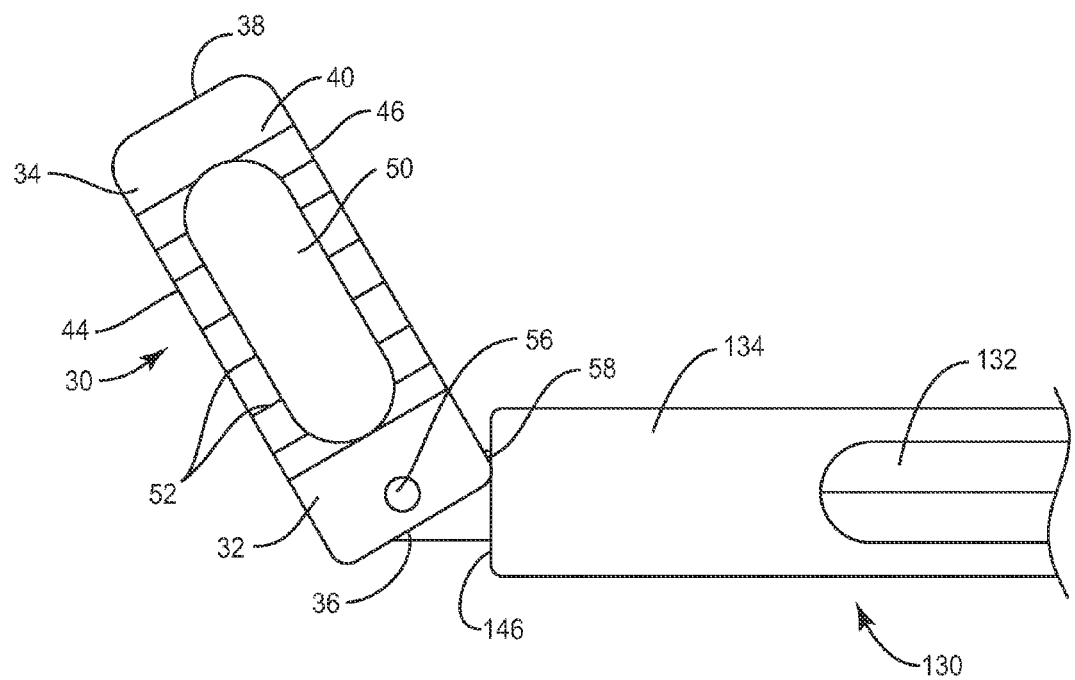
FIG. 7 is a top, break away view of the implant and the instrument shown in FIG. 2.

Implant 30 may be unlocked from instrument 130 by disengaging interface 146 of instrument 130 from engagement surface 58 of implant 30, while catch 56 remains captured by capture surface 140, allowing implant 30 to pivot about catch 56. It may become necessary to apply force to pivot implant 30. Indeed, because implant 30 is compressed between two vertebrae, it may be difficult to pivot using instrument 130. It is therefore desirable to apply a force directly to implant 30 to pivot the same to a desired angle or position. Applying force directly to the outside surface of implant 30 avoids the pivot force being applied directly to catch 56, which may have limited strength. To pivot implant 30 to the desired angle or position, capture surface 140 of instrument 130 is first inserted into recess 54 of implant 30 in an open position and is positioned to engage catch 56 within cavity 150. Capture surface 140 is then moved to a closed position, which captures catch 56 within cavity 150. Instrument 130 may be pivoted at multiple angles relative to a longitudinal axis $a^2$ of instrument 130 by applying a force to a surface of implant 30, such as side surface 44 or side surface 46 such that implant 30 pivots about catch 56. As shown in FIG. 7, engagement surface 58 of implant 30 is positioned on a corner of implant 30 between proximal face 36 and side surface 46; and implant 30 is pivoted approximately 45° relative to longitudinal axis $a^2$ defined by instrument 130. After implant 30 is pivoted to a desired orientation, interface 146 is moved distally relative to instrument 130 until interface 146 contacts engagement surface 58 of implant 30. After contacting implant 30, distal face 148 may push implant 30 such that implant 30 pivots about catch 56 in the axial plane to a desired angle or position.

Figure 8:
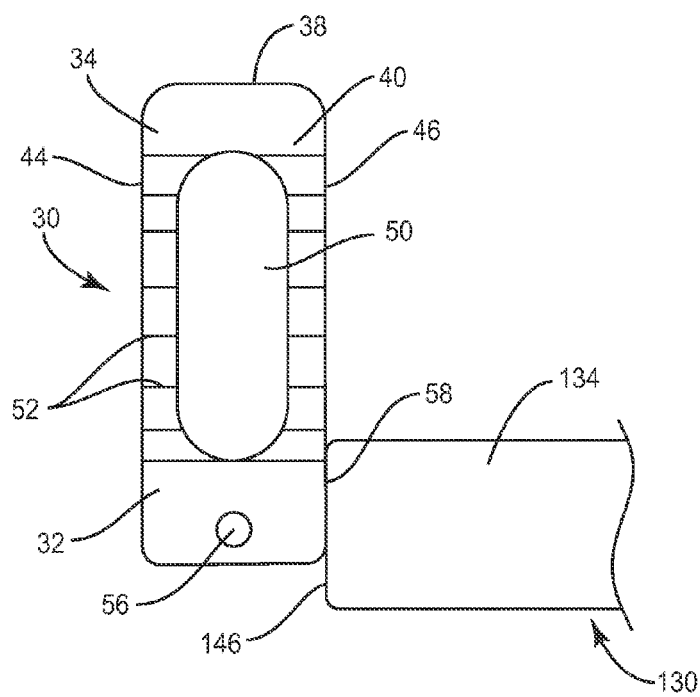
FIG. 8 is a top, break away view of the implant and the instrument shown in FIG. 2.

As shown in FIG. 8, engagement surface 58 may be located on a side surface such as side surface 46, where side surface 46 is planar. Implant 30 may be locked to instrument 130 in a 90° orientation relative to a longitudinal axis $a^2$ of instrument 130 such that implant 30 may be inserted between two adjacent vertebrae leading with a side surface, such as side surface 44. To insert implant 30 into an intervertebral space with implant 30 locked to instrument 130 in a 90° orientation relative to a longitudinal axis $a^2$ of instrument 130, capture surface 140 is inserted into recess 54 of implant 30 in an open position and is positioned to engage catch 56 within cavity 150. Capture surface 140 is then moved to a closed position, which captures catch 56 within cavity 150. Implant 30 may then be pivoted 90° such that side surface 46 is perpendicular to interface 146. To lock implant 30 in a 90° orientation relative to a longitudinal axis $a^2$ of instrument 130, distal face 148 of second member 134 is advanced toward side surface 46 of implant 30 until interface 146 of second member 134 engages side surface 46 to releasably lock implant 30 in a 90° orientation, thereby preventing implant 30 from rotating within instrument 130. Implant 30 may then be inserted into an intervertebral space in a 90° orientation, leading with side surface 44.

Figure 9:
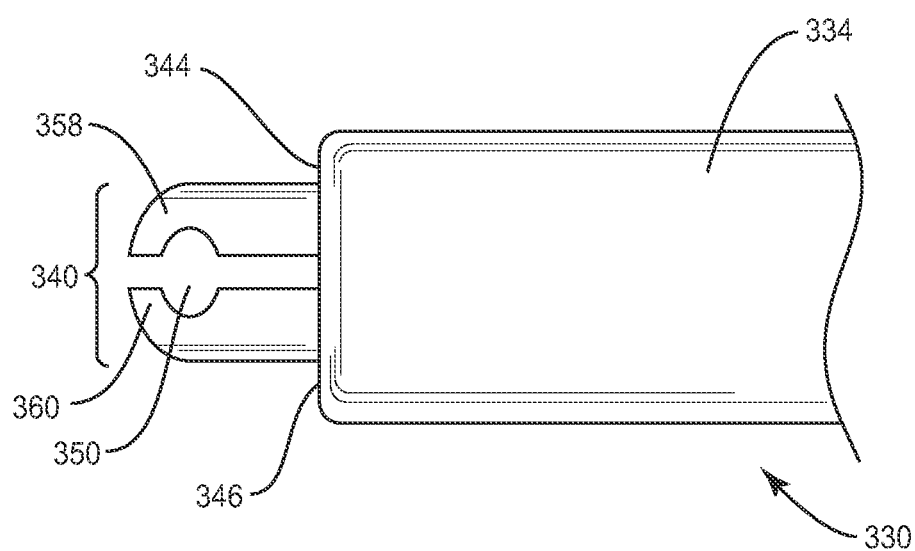
FIG. 9 is a top, break away view of an instrument in accordance with the principles of the present disclosure.

In one embodiment, shown in FIG. 9, the interbody implant system includes an instrument 330 which has a similar configuration to instrument 130 and includes a first member 332 and a second member 334 that is movable relative to first member 332. First member 332 includes a capture surface 340 at the distal end thereof configured to engage a catch, such as catch 56 of implant 30. The distal end of first member 332 is bifurcated longitudinally into opposing claws 358, 360 that define a cavity 350 for receiving catch 56 and are movable to fix catch 56 in cavity 350. Opposing claws 358 and 360 extend from the distal end of second member 332 a first distance, which is less than the depth of recess 54 such that when capture surface 340 is inserted into recess 54, capture surface 340 may engage catch 56 and pivot about catch 56 without contacting the sides of recess 54, thus allowing instrument 330 to freely pivot about catch 56. Cavity 350 is cylindrical to facilitate capture of a cylindrical pin, such as catch 56, while providing space for catch 56 to pivot within cavity 350. Catch 56 may be positioned within cavity 350 when capture surface 340 is in an open position. Capture surface 340 then moves to a closed position by converging opposing claws 358, 360, which allows implant 30 to pivot about catch 56 to a plurality of orientations. Second member 334 includes a distal end 344 having an interface 346 configured to engage engagement surface 58 of implant 30 to releasably lock implant 30 in at least one orientation relative to second member 334.

Figure 10:
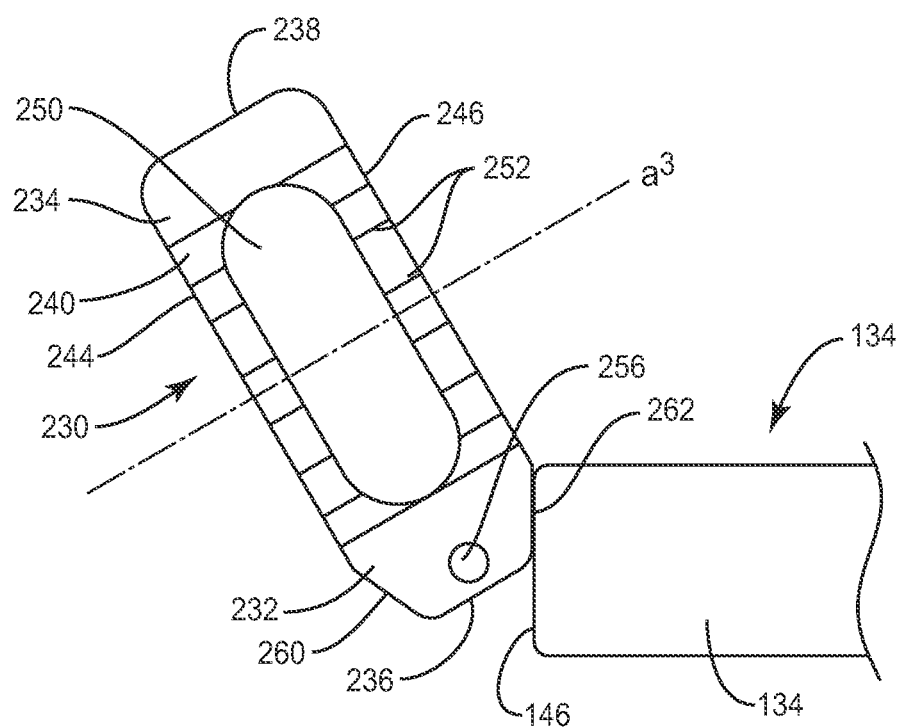
FIG. 10 is a top view of an implant in accordance with the principles of the present disclosure and a break away view of the instrument shown in FIG. 2.

As discussed above, the system of the present invention allows pivoting of an implant in an intervertebral space. Indeed, when surgeons perform an interbody fusion via a posterior approach, some like to pivot an implant in the axial plane so that a side surface of the implant faces anteriorly. This approach allows the surgeon to avoid areas of the spinal column, such as the spinal cord, as desired, while performing posterior spinal fusion. In one embodiment, shown in FIG. 10, the interbody implant system includes an implant 230 configured to be inserted between adjacent vertebrae which is similar in configuration to implant 30 and includes a proximal end 232, a distal end 234 opposite proximal end 232, an upper surface 240, a lower surface (not shown), and side surfaces 244, 246. Proximal end 232 includes a proximal face 236, while distal end 234 includes a distal face 238. Upper and lower surfaces 240, 242 are configured to interface with load bearing endplates of adjacent vertebrae, while side surfaces 244, 246, proximal end 232 and distal end 234 extend between upper and lower surfaces 240, 242. Upper and lower surfaces 240, 242 include bone engaging features 252 configured to reduce slipping or movement relative to the vertebrae implant 230 is placed between. A hollow center 250 opening at upper and lower surfaces 240, 242 allows placement of materials, such as bone growth materials, to promote bonding and/or fusion of implant 230 to adjacent vertebrae. Implant 230 includes at least one recess (not shown) in proximal end 232 disposed in a parallel orientation relative to a transverse axis $a^3$ of implant 230 that extends along side surfaces 244, 246 configured to receive at least a portion of an insertion instrument, such as instrument 130. The recess includes a catch 256, such as a cylindrical pin, which is configured to be captured by instrument 130. Implant 230 further includes at least one surface configured to engage instrument 130, to lock the rotation of implant 230 within instrument 130. Proximal face 236 includes a first lateral face 260 that converges with proximal face 236 to form a first angle and a second lateral face 262 that converges with proximal face 236 to form a second angle. Either proximal face 236, first lateral face 260, or second lateral face 262 may act as an engagement surface to engage an engaging portion of an instrument, such as interface 146 of instrument 130. Implant 230 is pivotable relative to second member 234 via engagement of second member 234 with at least one of the first and second angles. As shown in FIG. 10, first lateral face 260 and second lateral face 262 are each disposed at an angle relative to proximal face 236. It is envisioned that lateral faces 260, 262 may each be disposed at a variety of angles (from 0 to 90° and from 0 to −90°) relative to proximal face 236.

To insert implant 230 into an intervertebral space at the first angle, capture surface 140 of instrument 130 is inserted into the recess in proximal end 232 of implant 230 in an open position and is moved to engage catch 256. Capture surface 140 is then moved to a closed position, which captures catch 256 within cavity 150 such that implant 230 may pivot about catch 256. Implant 30 is then pivoted about catch 256 until second lateral face 262 and interface 146 of instrument 130 are substantially parallel to one another. Implant 230 may be locked to instrument 130 by advancing interface 146 of instrument 130 toward second lateral face 262 of implant 230 until interface 146 engages second lateral face 262 to releasably lock implant 230, thereby preventing implant 230 from pivoting about catch 256. Implant 30 may then be inserted into an intervertebral space at an angle equal to the first angle. Likewise, to insert implant 230 into an intervertebral space at the second angle, capture surface 140 of instrument 130 is inserted into the recess in proximal end 232 of implant 230 in an open position and is moved to engage catch 256. Capture surface 140 is then moved to a closed position, which closes catch 256 within cavity 150 in a manner that permits implant 230 to pivot about catch 256. Implant 30 is then positioned at the second angle by pivoting implant 230 about catch 256 until first lateral face 260 and interface 146 of instrument 130 are substantially perpendicular to one another. Implant 230 may be locked to instrument 130 at the second angle by advancing interface 146 toward first lateral face 260 until interface 146 engages first lateral face 260 to releasably lock implant 230, thereby preventing implant 230 from pivoting about catch 256. Implant 30 may then be inserted into an intervertebral space at an angle equal to the second angle.

An alternative way to insert implant 230 into an intervertebral space comprises locking implant 230 in a straight orientation with the inserting tool so that the implant 230 can be inserted into the disc space. The implant 230 is then unlocked form the straight orientation in which it was inserted by moving the capture surface 140 to a closed position, which closes catch 256 within cavity 150 in a manner that permits implant 230 to pivot about catch 256. Implant 230 is then positioned at the second angle by pivoting implant 230 about catch 256. Once in the second position the implant 230 is re-locked by advancing interface 146 toward first lateral face 260 until interface 146 engages first lateral face 260 to releasably lock implant 230, thereby preventing implant 230 from pivoting about catch 256. The implant 230 can then be positioned into the desired location and orientation.

Figure 11:
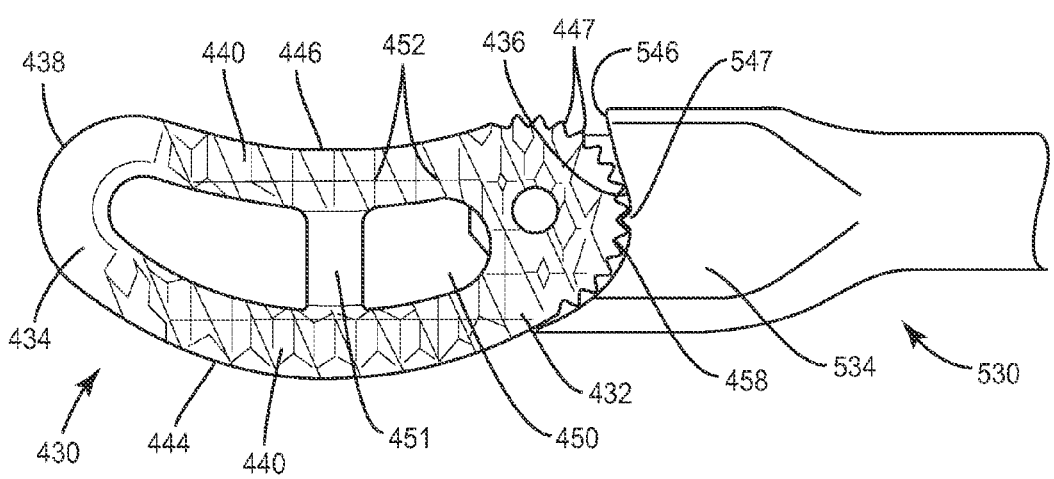
FIG. 11 is a top, break away view of an implant and an instrument in accordance with the principles of the present disclosure.

In one embodiment, shown in FIG. 11, the interbody implant system includes an implant 430, which is similar to implant 30 and implant 230, having a proximal end 432, a distal end 434 opposite proximal end 432, an upper surface 440, a lower surface 442 (not shown) opposite upper surface 440 and having a configuration similar to upper surface 440, and side surfaces 444, 446. Implant 430 assumes a generally annular kidney-shape, corresponding to the annular kidney-shape of the anterior aspect of the vertebra. Proximal end 432 includes a proximal face 436, while distal end 434 includes a distal face 438. Upper and lower surfaces 440, 442 are configured to interface with load bearing endplates of adjacent vertebrae, while side surfaces 444, 446, proximal end 432 and distal end 434 extend between upper and lower surfaces 440, 442. Upper and lower surfaces 440, 442 include bone engaging features 452 configured to reduce slipping or movement relative to the vertebrae implant 430 is placed between. Implant 430 includes a hollow center 450 disposed in a perpendicular orientation relative to longitudinal axis $a^4$ of implant 430 and configured to allow placement of materials, such as bone growth materials, to promote bonding and/or fusion of implant 430 to adjacent vertebrae. As shown in FIG. 11, implant 430 includes a stabilizer 451 extending between side surfaces 444, 446 and bisecting hollow center 450 to provide stability to implant 430. Implant 430 further includes at least one engagement surface 458 configured to engage instrument 530, to lock the rotation of implant 430 within instrument 530. Engagement surface 458 has a smooth arcuate configuration that defines a first radius of curvature. Proximal face 436 includes at least one protrusion, such as an angled tooth.

In addition to implant 430, the system of the present invention also includes an instrument 530 is configured to engage implant 430, pivot implant 430 relative to instrument 530, lock implant 430 at a particular angle relative to instrument 530 and insert implant 430 at the desired angle. Instrument 530 includes a second member 534 having an interface 546 with a smooth, arcuate configuration that defines a second radius of curvature and is configured to capture implant 430. The second radius of the curvature is less than the first radius of curvature such that interface 546 engages engagement surface 458 in an interference fit to releasably lock implant 430 in at least one orientation relative to first member 532. The at least one protrusion 447 on proximal face 436 is/are constructed of a first material while instrument 530 is constructed of a second material, the second material being harder than the first material such that protrusions 447 deform when pressed into interface 546 to lock implant 430 in place at a particular angle relative to instrument 530. In one embodiment, engagement surface 458 has a plurality of protrusions 447 which resemble gear teeth extending from the proximal end of side surface 444 across proximal face 436 and the proximal end of side surface 446. Any of the protrusions 447 along side surface 444, proximal face 436 or side surface 446 may be used to engage interface 546 of instrument 530 to attach implant 430 to instrument 530 along side surface 444, proximal face 436 or side surface 446, thus permitting implant 430 to attach to instrument 430 at many different angles, which in turn permits implant 430 to be implanted between two adjacent vertebrae at many different angles, using different approaches. In one embodiment, instrument 530 includes gear teeth 547 on interface 546 configured to engage protrusion(s) 447 of implant 430 such that gear teeth 547 mesh with at least one protrusion 447 to lock the rotation of implant 430 within instrument 530 at a particular angle relative to first member 532.

Figure 12:
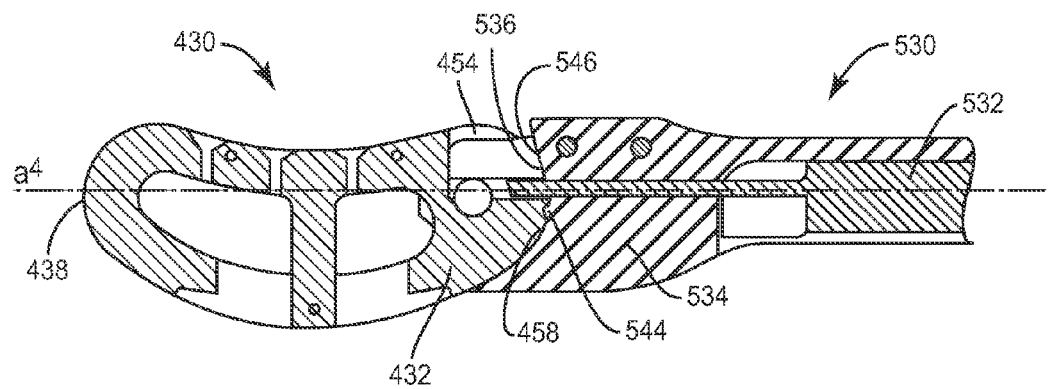
FIG. 12 is a top, break away view of an implant and an instrument in accordance with the principles of the present disclosure.
Figure 13:
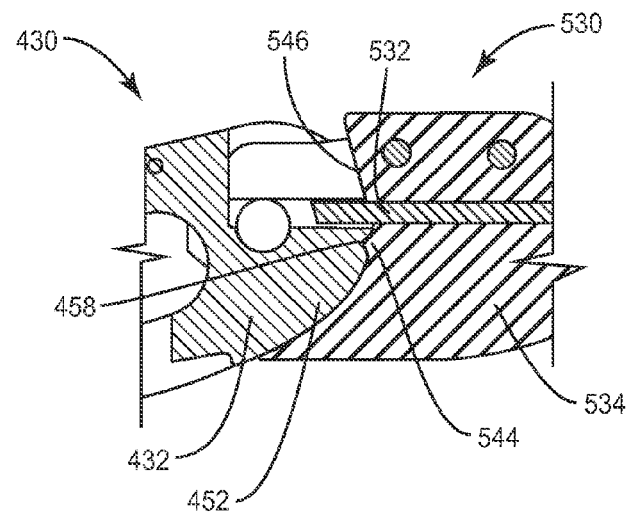
FIG. 13 is an enlarged detail view of the implant and instrument shown in FIG. 12.

In one embodiment illustrated in FIGS. 12 and 13, instrument 530 may have at least one locking protrusion 544 that is configured to engage a corresponding recess 458 in implant 430 to maintain implant 430 at a particular angle relative to instrument 530 by preventing implant 430 from rotating within instrument 530. It is envisioned that locking protrusion 544 may be larger than recess 458 to which it corresponds. Instrument 530 may be made of a material that is harder than the material implant 430 is made of, such that locking protrusion 544 will deform the softer recess 458 to lock implant 430 in place via an interference fit. Locking protrusion 544 has a convexly curved cross-sectional profile and recess 458 has a concave cross-sectional profile that corresponds to the curve of locking protrusion 544. Locking protrusion 544 may have a polygonal cross-sectional profile such as a triangular, rectangular (including square), heptagonal, hexagonal, etc. cross-sectional profile. Likewise, recess 458 may have a cross-sectional profile which corresponds to the polygonal cross-sectional profile of locking protrusion 544 such that at least a portion of locking protrusion 544 fits within recess 458 to maintain implant 430 at a particular angle by preventing implant 430 from rotating within instrument 530. Locking protrusion 544 may be an angled tooth that engages a corresponding recess 458 such that implant 430 may be rotated in one direction only.

As illustrated in FIGS. 12 and 13, proximal face 436 has a portion that is convexly curved, as well as, a portion that is planar. Instrument 530 includes interface 546 which corresponds to the convexly curved portion of proximal face 436 so as to engage implant 430 with instrument 530 rotates implant 430 within recess 558 in one direction only. That is, when implant 430 is rotated within recess 558 such that the portion of the proximal face 436 that is convexly curved mates with concavely configured interface 536 of the instrument 530, implant 430 moves freely within recess 558. However, moving the implant 430 in the opposite direction engages the planar portion of the proximal face 436 with the concavely configured interface 536 and since the planar portion of the proximal face 436 of the implant cannot move freely against the concavely configured interface 536, movement of the implant 430 in restricted to one direction only. Instrument 530 may have a plurality of locking protrusions 544 configured to engage corresponding recesses 458 in implant 430 to maintain implant 430 at different angles relative to instrument 530.

In one embodiment, instrument 530 includes a first member 532 extending longitudinally through second member 534 and out from an opening in a distal end of second member 534. Second member 534 includes an inner hollow portion. First member 532 has a transverse dimension which is less than the inner hollow portion of second member 534, such that first member 532 extends through the inner hollow portion of second member 534 and out from an opening in the distal end of second member 534. Proximal end 432 includes at least one recess 454 sized and configured to receive at least a portion of first member 532. As illustrated in FIGS. 12 and 13, recess 454 is formed by cutting out a rectangular piece from the upper right corner of upper surface 440, including at least a portion of proximal end 432 and at least a portion of side surface 446. In particular, recess 454 is formed by making a first cut in the proximal end of side surface 446 which is perpendicular to longitudinal axis $a^4$ of implant 430. Next, a second cut is made in proximal end 432 between side surfaces 444, 446. The second cut is parallel to longitudinal axis $a^4$ of implant 430. The first and second cuts define an area of recess 454. Recess 454 may extend downward from upper surface 440 a distance between upper and lower surfaces 440, 442. Recess 454 terminates prior to reaching lower surface 442 so as not to extend through upper and lower surfaces 440, 442. It is envisioned that recess 454 may be triangular, square, pentagonal, hexagonal, or any other polygonal shape. Alternatively, recess 454 may have a round or oval shape. Recess 454 has a length extending along a longitudinal axis $a^4$ of implant 430 extending from proximal end 432 toward distal end 434 that terminates before distal end 434. The length of recess 454 should be sufficient to permit instrument 530, to engage implant 430 and pivot implant 430 axially. Accordingly, the length of recess 454 is slightly larger than an engaging portion of instrument 530. To engage implant 430, first member 532 of instrument 530 is extended through the opening in the distal end of second member and into recess 454. Implant 430 may be rotated within interface 546 until first member 532 engages the first cut or the second cut that define an area of recess 454. First member 532 engaging a linear edge of recess 454 prevents implant 430 from moving relative to instrument 530.

Figure 14:
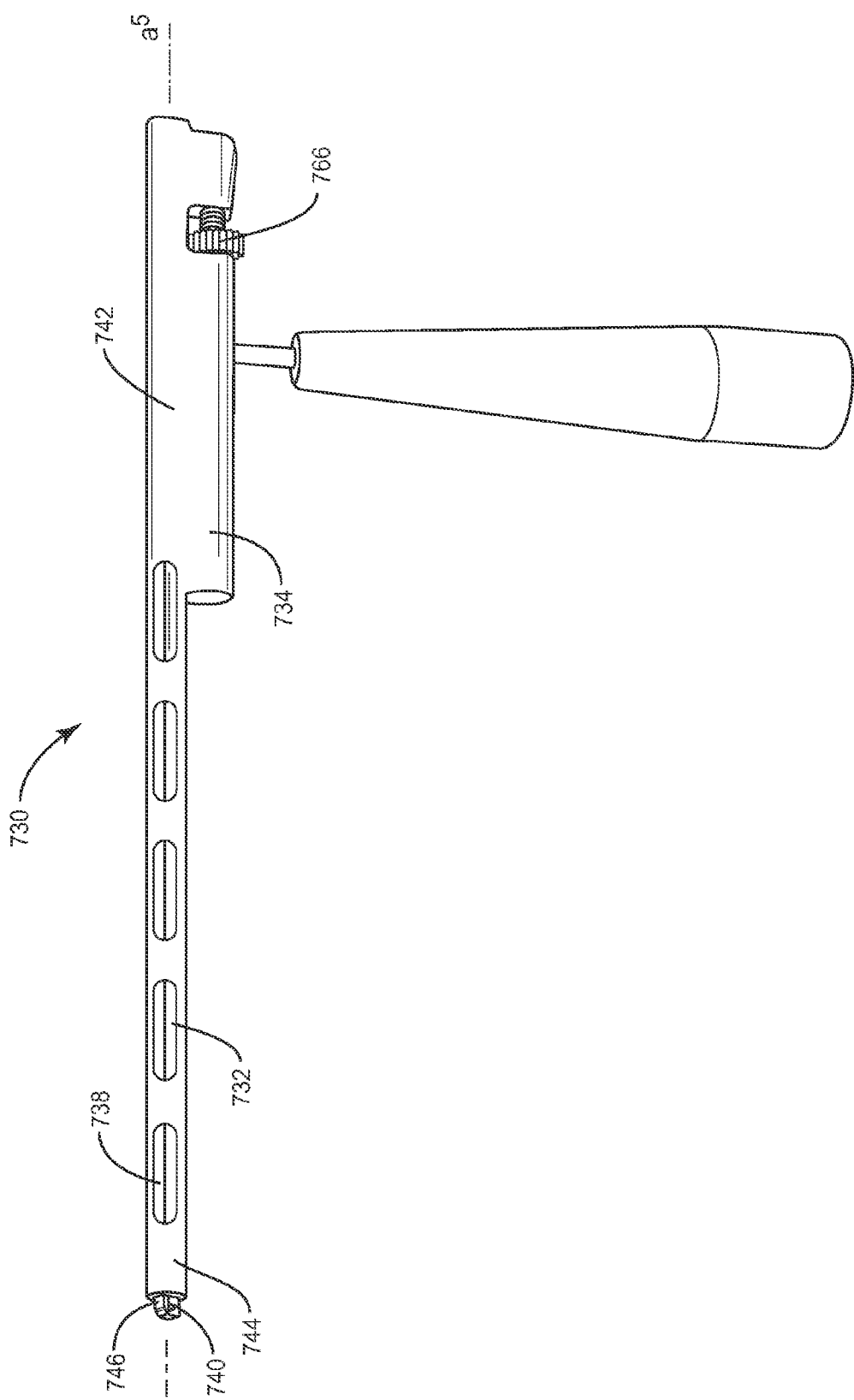
FIG. 14 is a perspective view an instrument implant and an instrument.
Figure 15:
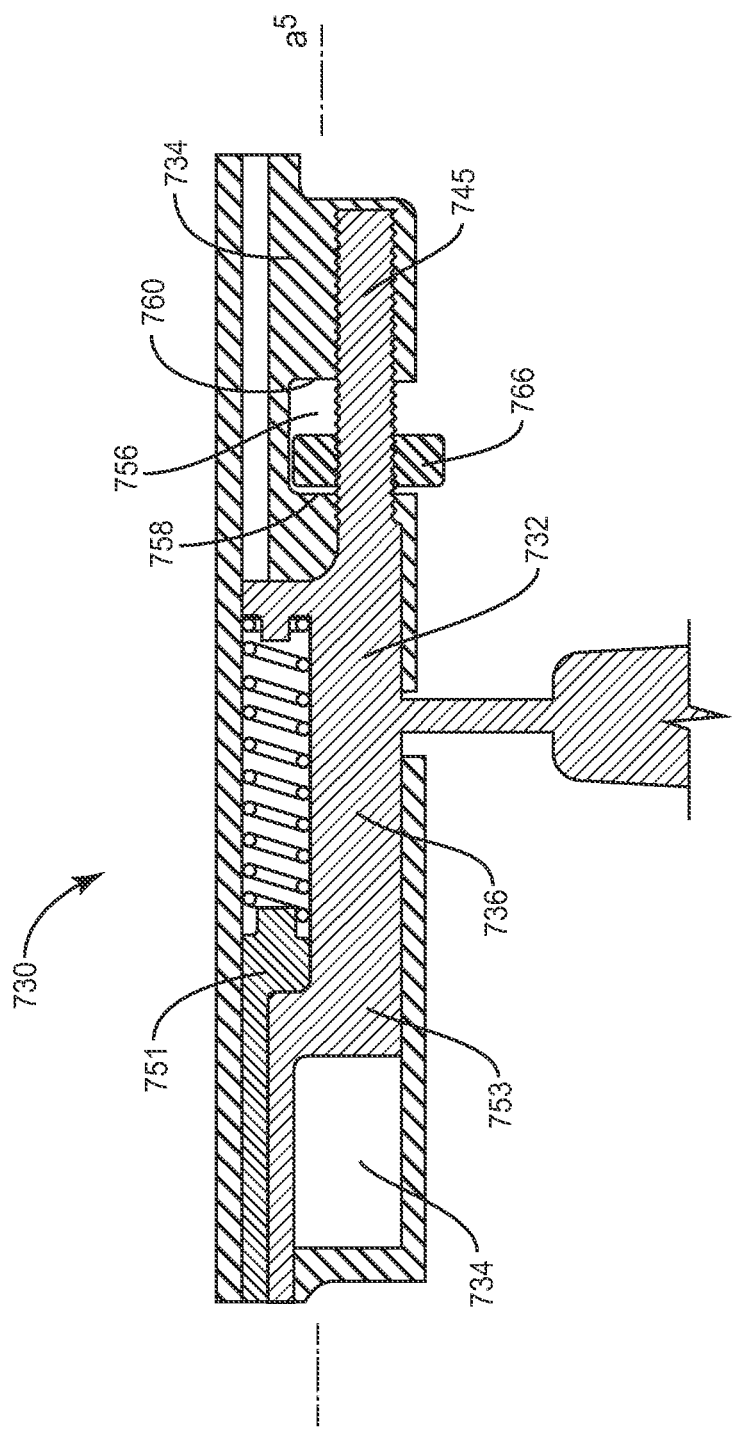
FIG. 15 is an enlarged side, cutaway view of the instrument shown in FIG. 14.
Figure 16:
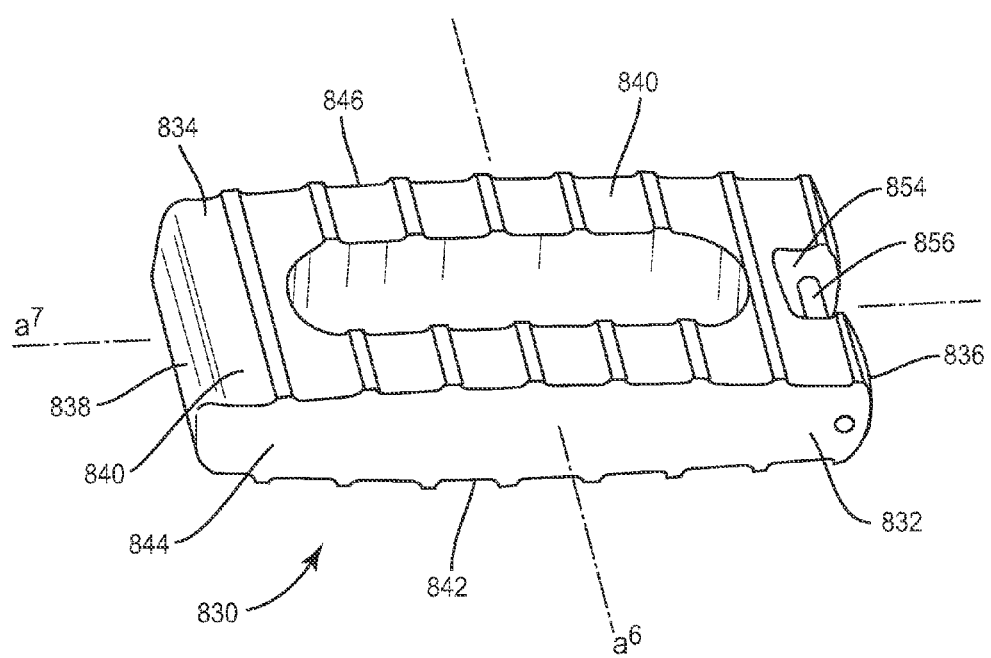
FIG. 16 is a perspective view of an implant in accordance with the principles of the present disclosure.
Figure 17:
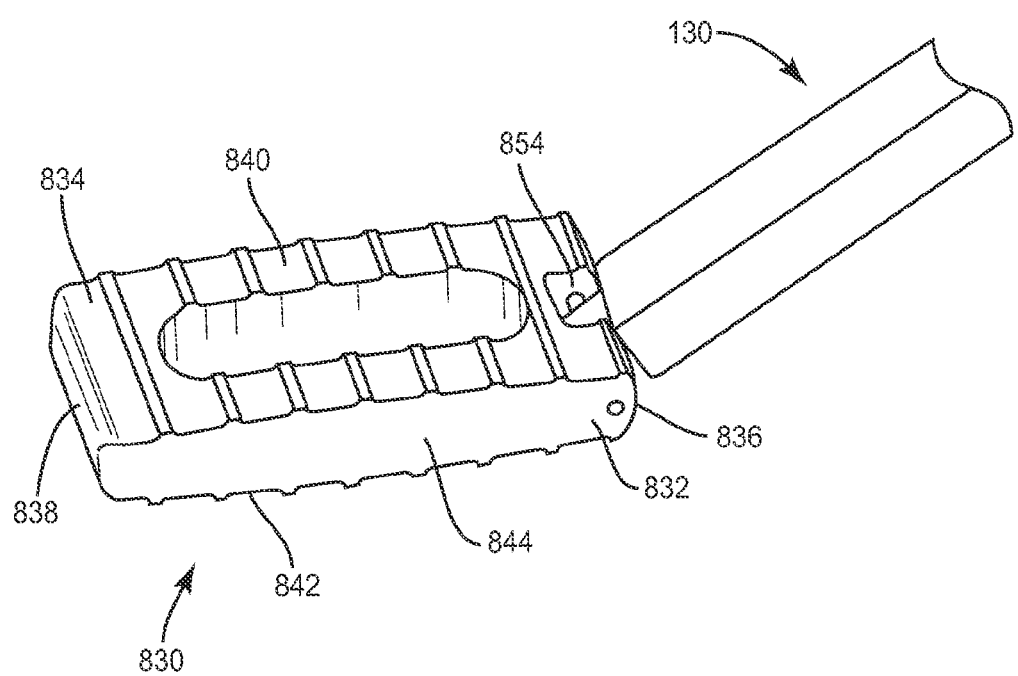
FIG. 17 is a perspective view of the implant shown in FIG. 16 and a break away view of an instrument of the system.
Figure 18:
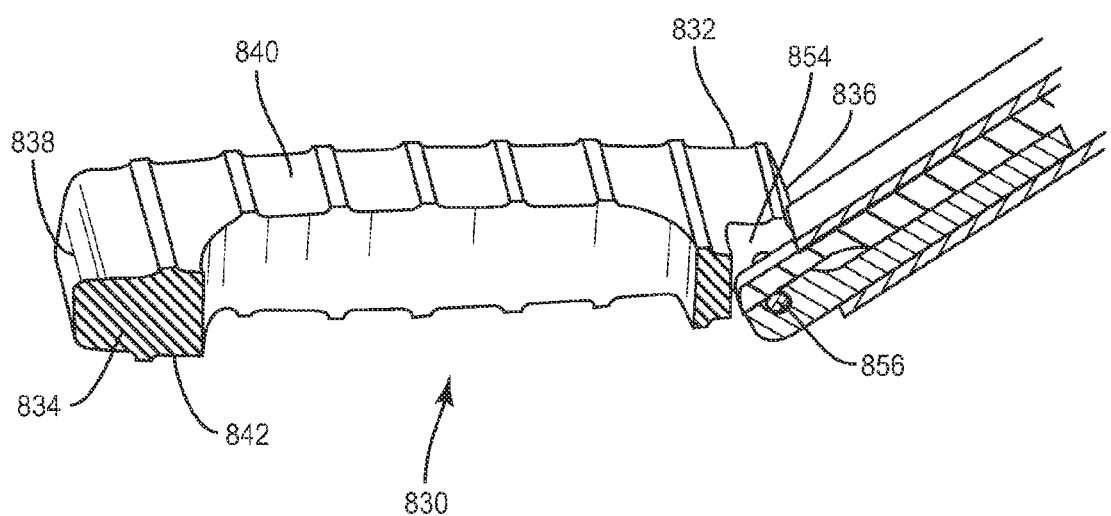
FIG. 18 is a cross-sectional perspective view of the implant and instrument shown in FIG. 17.
Figure 19:
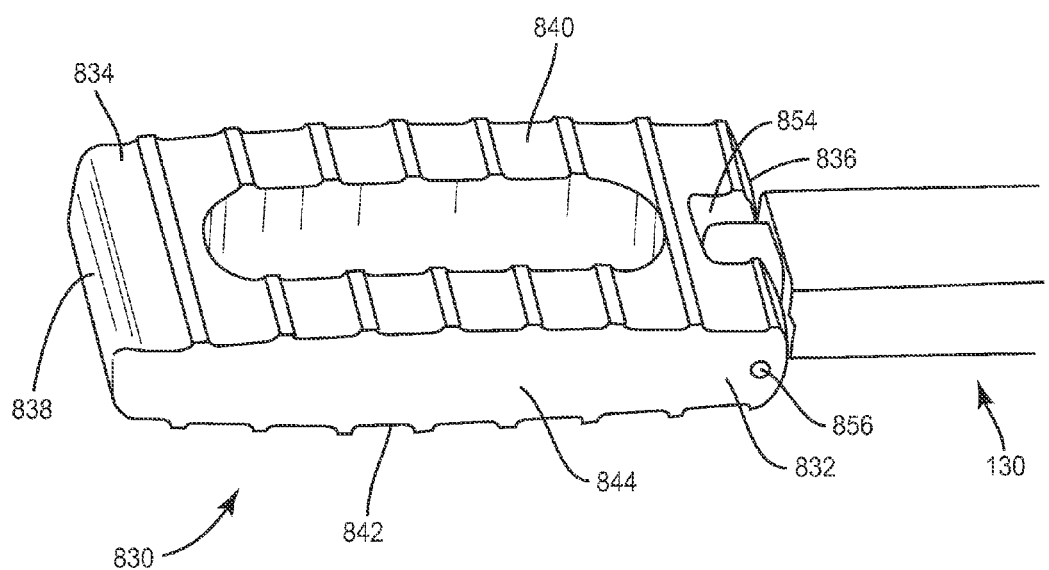
FIG. 19 is a perspective view of the implant and instrument shown in FIG. 17.
Figure 20:
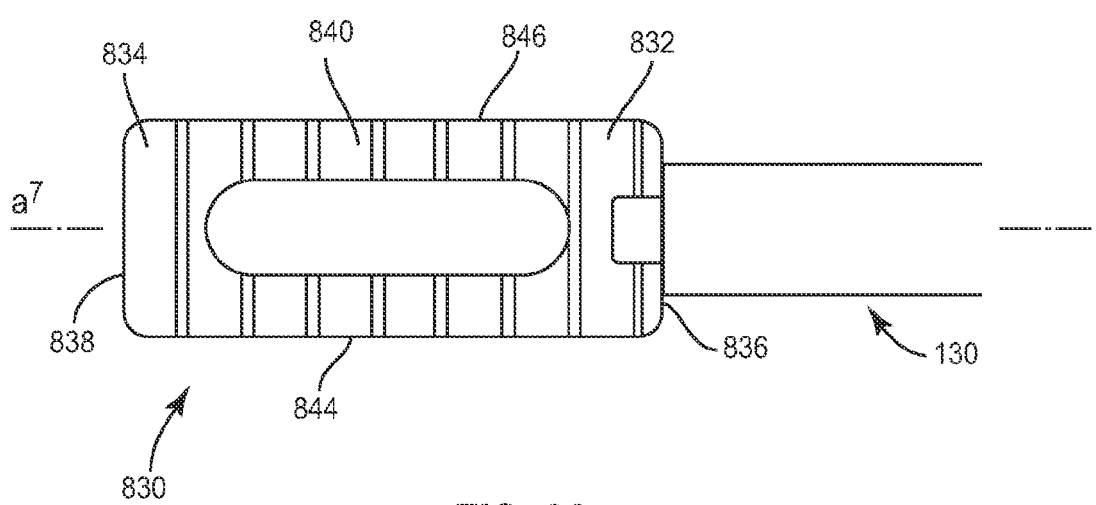
FIG. 20. is a top view of the implant and a break away view of the instrument shown in FIG. 17.
Figure 21:
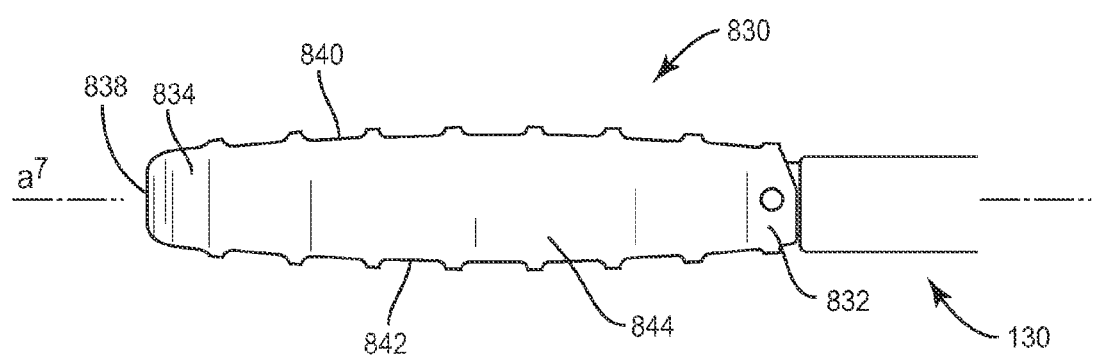
FIG. 21 is a side view of the implant and a break away view of the instrument shown in FIG. 17.

In one embodiment, illustrated in FIGS. 14 and 15, the system of the present invention includes an instrument 730 having a similar configuration to instruments 130, and 530, but includes a capture surface 740 that may be translated between open and closed positions via rotation of a threaded surface 745 of a first member 732. Instrument 730 includes a first member 732 and a second member 734 that is movable relative to first member 732. Second member 734 is a sleeve configured to fit about first member 732 and has an opening in a distal end thereof through which first member 732 may extend. It is envisioned that first member 732 and/or second member 734 may be rectangular, cylindrical, or, in the alternative, may have other cross section shapes such as square, hexagonal or octagonal, for example. Second member 734 includes at least one recess 756 disposed within second member 734 in a perpendicular orientation relative to longitudinal axis $a^5$ of instrument 730 defined by a first wall 758 and a second wall 760.

First member 732 includes a proximal end 736 and a distal end 738 having a capture surface 740 configured to engage a catch, such as catch 56 of implant 30, for example. First member 732 is bifurcated longitudinally into a top portion 751 and a bottom portion 753 that is movable relative to top portion 751. In one embodiment, top portion 751 is spring loaded such that top portion 751 moves relative to bottom portion 753 via a spring that will translate top portion 751 distally, relative to bottom portion 753. A hook is fixed to the distal end of top portion 751 and a gate is fixed the distal end of bottom portion 753. The hook defines a cavity configured to receive a catch such that implant may pivot about the catch when the catch is received within the cavity of the hook. Proximal end 736 includes a threaded surface 745 on the top and/or bottom portions of proximal end 736 and a wheel 766 having a bore extending through the center thereof having threads which correspond to threaded surface 745 such that threaded surface 745 may be threaded through the bore in wheel 766. Wheel 766 has a size and shape configured to fit within recess 756 of second member 734. As wheel 766 is turned in a first direction, such as clockwise, wheel 766 is moved distally along threaded surface 745 until wheel 766 engages first wall 758 of recess 756. Turning wheel 766 clockwise while engaged with first wall 758 causes bottom portion 753 of first member 732 with the gate fixed to the distal end thereof to move distally, translating the gate over at least a portion of the cavity within the hook, as the hook remains stationary. As wheel 766 is turned in a second direction, such as counterclockwise, wheel 766 is moved proximally along threaded surface 745 until wheel 766 engages second wall 760 of recess 756. Turning wheel 766 counterclockwise while engaged with second wall 760 causes bottom portion 753 of first member 732 with the gate fixed to the distal end thereof to move proximally, withdrawing the gate from at least a portion of the cavity within the hook, as the hook remains stationary.

Second member 734 includes a proximal end 742 and a distal end 744 having an interface 746 configured to engage an engagement surface, such as engagement surface 58 of implant 30, to releasably lock implant 30 in at least one orientation relative to second member 734. Interface 746 and engagement surface 58 each include at least one planar face such that interface 746 could be positioned perpendicarly against engagement surface 58, when capture surface 740 engages catch 56, to lock implant 30 at an angle relative to instrument 730 by preventing implant 30 from pivoting about catch 56. As wheel 766 is turned clockwise, second member 736 is moved distally until interface 746 engages an engagement portion 58 of implant 30.

In one embodiment, illustrated in FIGS. 16-25, the system of the present invention includes an implant 830, which is similar in configuration to implant 30, implant 230 and implant 430. Implant 830 includes a first end, such as proximal end 832, and a second end, such as distal end 834, opposite proximal end 832, upper and lower surfaces 840, 842, and side surfaces 844, 846. Implant 830 has a height defined by the distance between two adjacent vertebrae and a width defined by the distance between proximal end 832 and distal end 834. The width of implant 830 is approximately the width of at least one of the vertebrae implant 830 is positioned between. Proximal end 832 includes a proximal face 836, while distal end 834 includes a distal face 838. Upper and lower surfaces 840, 842 are configured to interface with load bearing endplates of adjacent vertebrae, while side surfaces 844, 846, proximal end 832 and distal end 834 extend between upper and lower surfaces 840, 842. In one embodiment, proximal face 836 is planar while distal face 838 is convexly curved between upper and lower surfaces 840, 842 and is configured to allow at least a portion of distal face 838 to be inserted into a collapsed, undistracted disc space. However, it is envisioned that distal face 838 may also be pointed, planar or concavely curved between upper and lower surfaces 840, 842.

Implant 830 includes at least one recess 854 disposed in proximal end 832 in a perpendicular orientation relative to transverse axis $a^6$ of implant 830. Recess 854 is sized and configured to receive at least a portion of an insertion instrument, such as instrument 130. In one embodiment recess 854 is rectangular, however it is envisioned that recess 854 may have a polygonal shape such as triangular, square, pentagonal, hexagonal, or may have a round or oval shape. Recess 854 extends through upper and lower surfaces 840, 842 and is disposed within proximal end 832 of implant 830 without extending through side surfaces 844, 846, such that recess 854 is disposed between side surfaces 844, 846. Recess 854 is disposed equidistant between side surfaces 844, 846, however it is envisioned that recess 854 may be disposed in proximal face 836 such that one side of recess 854 is closer to side surface 844 than the opposite side of recess 854 is from side surface 846, or vice versa.

Recess 854 includes a cylindrical pin, such as, for example, catch 856 disposed therein in a parallel orientation relative to transverse axis $a^6$ of implant 830 such that implant 830 can be pivoted about catch 856 in a coronal plane. Pivoting implant 830 about catch 856 in a coronal plane allows implant 830 to be inserted into the L4/L5 or L5/S1 disc space by angling down laterally from the top of the iliac crest. Catch 856 is configured to be captured by an instrument that facilitates positioning of spinal implant 830, such as instrument 130. In one embodiment, catch 856 extends through side surfaces 844, 846 in proximal end 832 of implant 830. However, it is envisioned that catch 856 may disposed in proximal end 832 of implant 830 without extending through side surfaces 844, 846. Catch 856 is disposed a distance from proximal end 832 extending along longitudinal axis $a^7$ of implant 830 toward distal end 834 which terminates before the inner portion of recess 854 such that an instrument, such as instrument 130, may engage implant 830 and pivot implant 830 about catch 856 without the instrument contacting the bottom of recess 854. In one embodiment, catch 856 is disposed equidistant between upper and lower surfaces 840, 842, however, it is envisioned that catch 856 may also be positioned such that the catch 856 is closer to upper surface 840 than lower surface 842, or vice versa.

Instrument 130 may engage implant 830 by capturing catch 856 within capture surface 140 such that implant 830 may pivot about catch 56, relative to instrument 830. In particular, capture surface 140 on the distal end of instrument 130 is inserted into recess 854 of implant 830 in an open position and is positioned to engage catch 856. Capture surface 140 is then moved to a closed position, which captures catch 856 within capture surface 140 such that implant 830 may pivot about catch 856 until implant is in a desired orientation relative to instrument 130. To lock implant 830 at the desired orientation, distal face 138 of instrument 130 is advanced toward implant 830 until distal face 138 engages proximal face 836 of implant 830 to releasably lock implant 830 in the desired orientation, thereby preventing implant 830 from rotating about catch 856. Implant 830 may then be inserted into an intervertebral space in the desired orientation, leading with proximal end 832.

Figure 22:
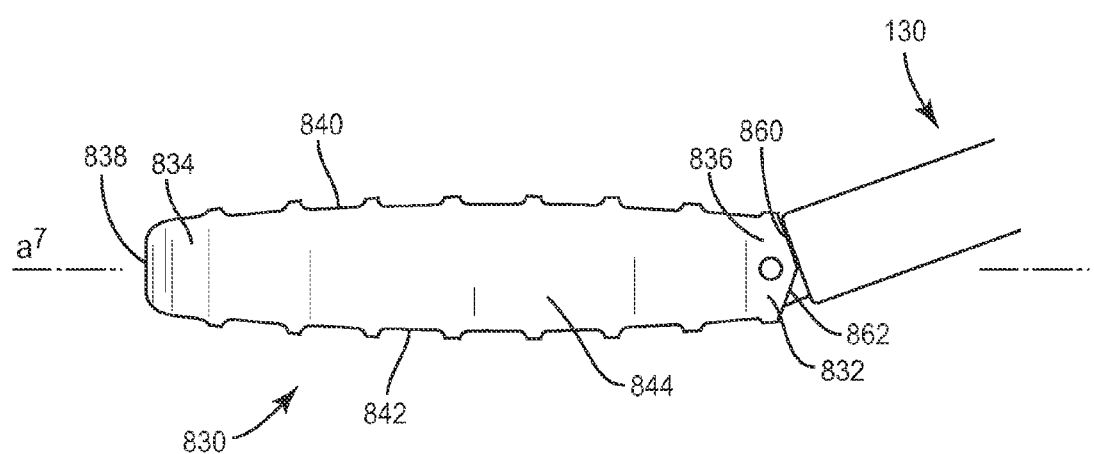
FIG. 22 is a side view of the implant and a break away view of the instrument shown in FIG. 17.

As shown in FIG. 22, proximal face 836 includes a first lateral face 860 that converges with proximal face 836 to form a first angle relative to longitudinal axis $a^7$ of implant 830 and a second lateral face 862 that converges with proximal face 836 to form a second angle relative to longitudinal axis $a^7$ of implant 830. Implant 830 is pivotable relative to second member 134 of instrument 130 via engagement of second member 134 with at least one of the first and second angles. In one embodiment, first lateral face 860 and second lateral face 862 are each disposed at the same angle relative to longitudinal axis $a^7$ of implant 830. However, it is envisioned that first lateral face 860 and second lateral face 862 may be disposed at different angles relative to longitudinal axis $a^7$ of implant 830. It is also envisioned that lateral faces 860, 862 may each be disposed at a variety of angles (from 0 to 90° and from 0 to −90°) relative to proximal face 836 such that implant 830 may be pivoted for insertion between adjacent vertebrae at a variety of angles using different approaches.

To insert implant 830 into an intervertebral space at the first angle, capture surface 140 of instrument 130 is inserted into recess 854 in proximal end 832 of implant 830 in an open position and is moved to engage catch 856. Capture surface 140 is then moved to a closed position, which closes catch 856 within cavity 150 in a manner that permits implant 830 to pivot about catch 856. Implant 830 is then positioned at the first angle, by pivoting implant 830 about catch 856 until first lateral face 860 and interface 146 of instrument 130 are substantially perpendicular to one another. Implant 830 may be locked to instrument 130 at the first angle by advancing distal face 138 of instrument 130 toward first lateral face 860 of implant 830 until interface 146 engages first lateral face 860 to releasably lock implant 830 at the first angle, thereby preventing implant 830 from rotating about catch 56. Implant 830 may then be inserted into an intervertebral space at an angle equal to the first angle, relative to instrument 130. Likewise, to insert implant 230 into an intervertebral space at the second angle, capture surface 140 of instrument 130 is inserted into recess 854 in proximal end 832 of implant 830 in an open position and is moved to engage catch 856. Capture surface 140 is then moved to a closed position, which closes catch 856 within cavity 150 in a manner that permits implant 830 to pivot about catch 856. Implant 830 is then positioned at the second angle by pivoting implant 830 about catch 856 until second lateral face 862 and interface 146 of instrument 130 are substantially perpendicular to one another. Implant 830 may be locked to instrument 130 at the second angle by advancing distal face 138 of instrument 130 toward second lateral face 862 of implant 830 until interface 146 engages second lateral face 862 to releasably lock implant 830 at the second angle, thereby preventing implant 830 from rotating about catch 856. Implant 830 may then be inserted into an intervertebral space at an angle equal to the second angle, relative to instrument 130.

Figure 23:
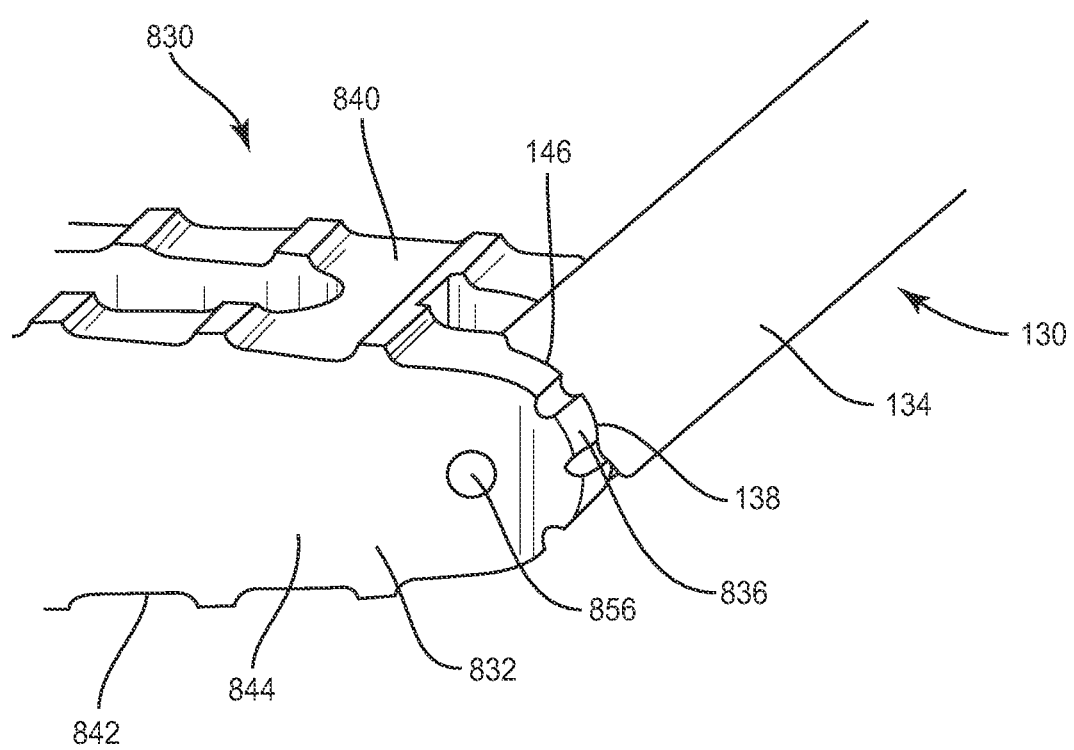
FIG. 23 is a break away perspective view of the implant and the instrument shown in FIG. 17.

In one embodiment shown in FIG. 23, proximal face 836 is convexly curved between upper and lower surfaces 840, 842 and interface 146 of instrument 130 has a curved geometry configured to mate with proximal face 836. Capture surface 140 of instrument 130 may be inserted into recess 854 in proximal end 832 of implant 830 in an open position and moved to engage catch 856 such that implant 830 may pivot about catch 856. Implant 830 is then positioned at the desired orientation relative to instrument 130. Implant 830 may be locked to instrument 130 at the desired orientation by advancing distal face 138 of instrument 130 toward proximal face 836 of implant 830 until interface 146 engages proximal face 836 to releasably lock implant 830 at the desired, thereby preventing implant 830 from rotating about catch 856. Implant 830 may then be inserted into an intervertebral space in the desired orientation. Protrusions and/or recesses on the distal face 138 can be used to lock the implant 830 at set angles once the distal face 138 is advanced towards the implant 830 and engages one of the protrusions/recesses that is associated with the orientation of implant 830.

Figure 24:
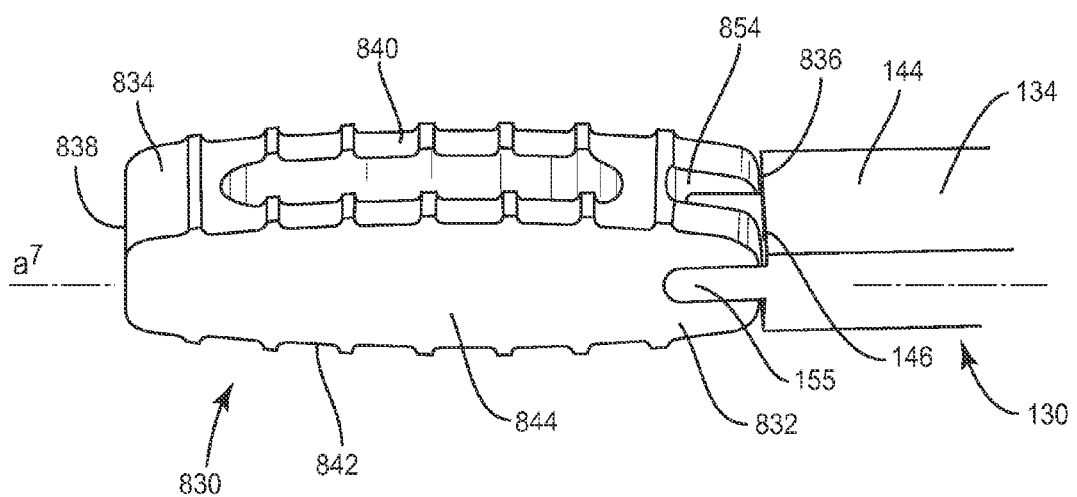
FIG. 24 is a perspective view of the implant and a break away perspective view of the instrument shown in FIG. 17.
Figure 25:
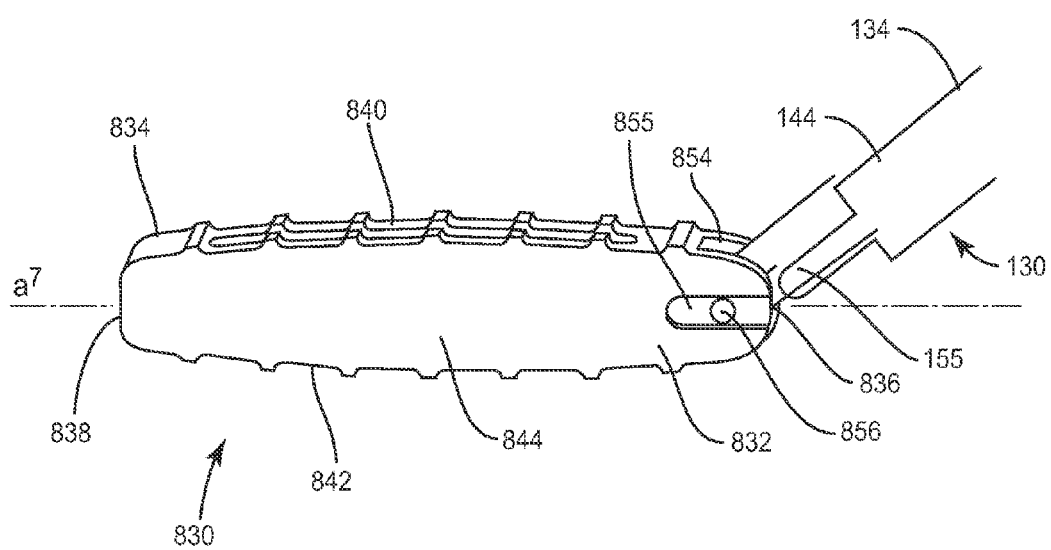
FIG. 25 is a side view of the implant and a side break away perspective view of the instrument shown in FIG. 17.

In one embodiment shown in FIGS. 24-25, implant 830 includes channels 855 extending along side surface 844 and side surface 846 a distance from proximal end 832 towards distal end 834 along the longitudinal axis $a^7$ of implant 830. Channels 855 are each configured to receive a locking tab on an instrument, such as instrument 130. Channels 855 are disposed equidistant between upper and lower surfaces 840, 842, however, it is envisioned that channels 855 may be disposed in proximal face 836 such that the top of channels 855 are closer to upper surface 840 than the bottom of channels 855 are from lower surface 842, or vice versa. Channels 855 have a depth extending longitudinally along longitudinal axis $a^7$ of implant 830 from proximal face 836 toward distal face 838 and terminates before distal face 838.

Second portion 134 of instrument 130 may include locking tabs 155 extending from distal end 144 of second portion 134 along the side surfaces thereof which are configured to be received within channel 855 on either side of implant 830 to secure implant 830 to instrument 130. In one embodiment, locking tabs 155 are disposed closer to the top surface of second portion 134 than the bottom surface. However it is also envisioned that locking tabs 155 may be disposed such that locking tabs 155 are closer to the bottom surface of second portion 134 than the top surface, or an equal distance form the top and bottom surfaces of second portion 134. The distance between locking tabs 155 is approximately equal to the distance between side surfaces 844, 846 of implant 830. More specifically, the distance between locking tabs 155 is approximately equal to the distance between channel 855 in side surface 844 and channel 855 in side surface 846. The length of locking tabs 155 is approximately equal to the depth of channels 855. Locking tabs 155 may be formed to at least partially elastically deform to engage implant 130 such that locking tabs 155 lock within channels 855. In particular, locking tabs 155 may be configured to elastically deform such that locking tabs 155 may be expanded so that the distance between locking tabs 155 is greater than the distance between channel 855 in side surface 844 and channel 855 in side surface 846. Locking tabs 155 are then positioned over channels 855, and then return to their original, non-expanded configuration, such that locking tabs 155 snap into place within channels 855. When locking tabs 155 are snapped into place within channels 855, interface 146 of instrument 130 engages proximal face 836 of implant 830 such that implant 830 is prevented from pivoting about catch 856.

Figure 26:
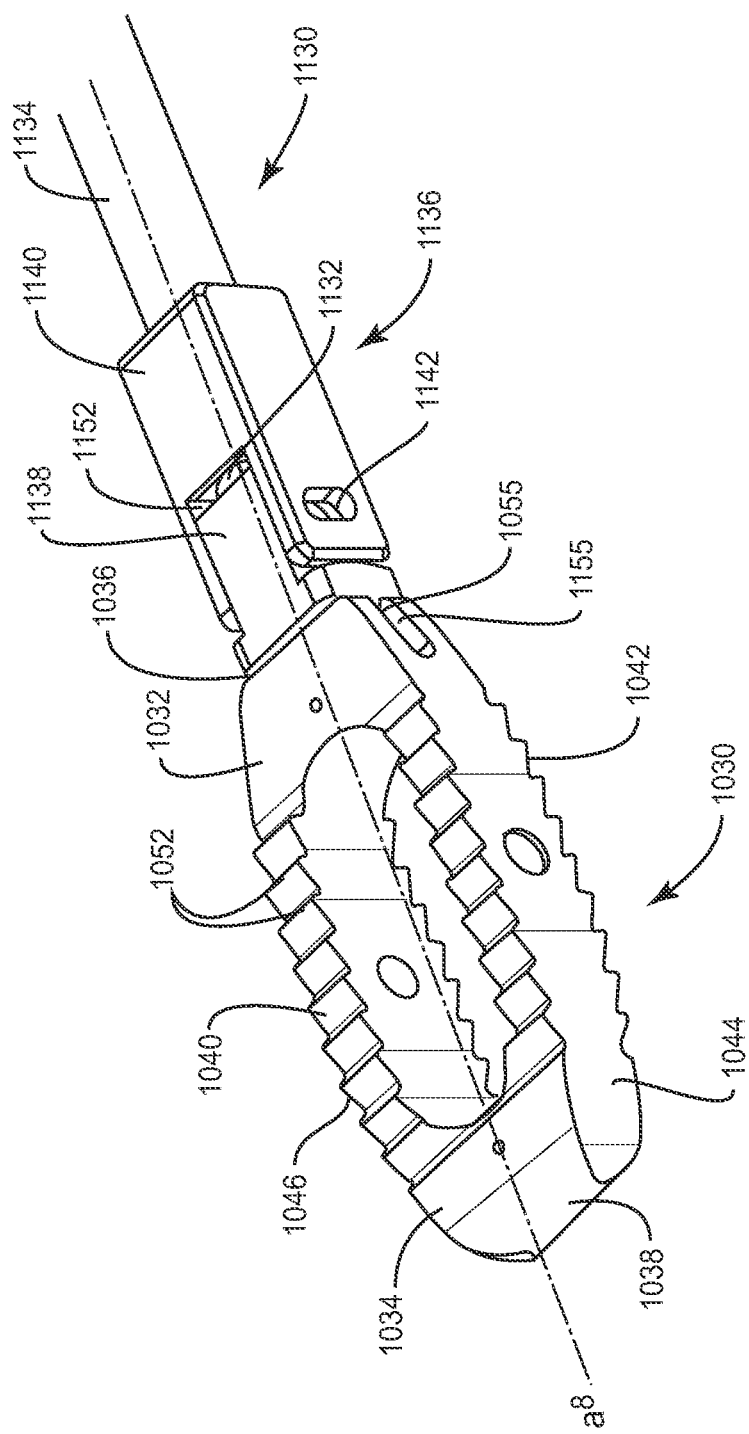
FIG. 26 is a perspective view of an implant of a system in accordance with the principles of the present disclosure and a break away view of an instrument of the system.
Figure 27:
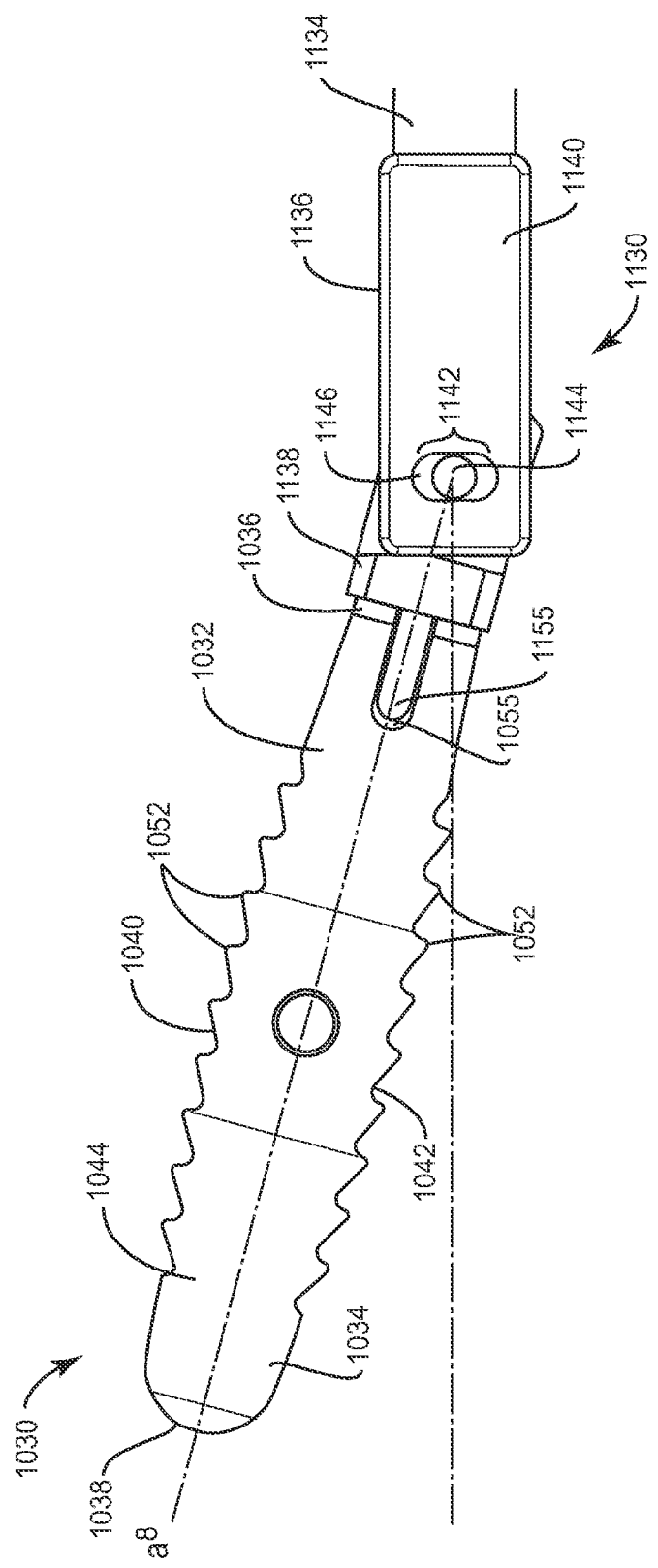
FIG. 27 is a side view of a portion of the instrument shown in FIG. 26.
Figure 28:
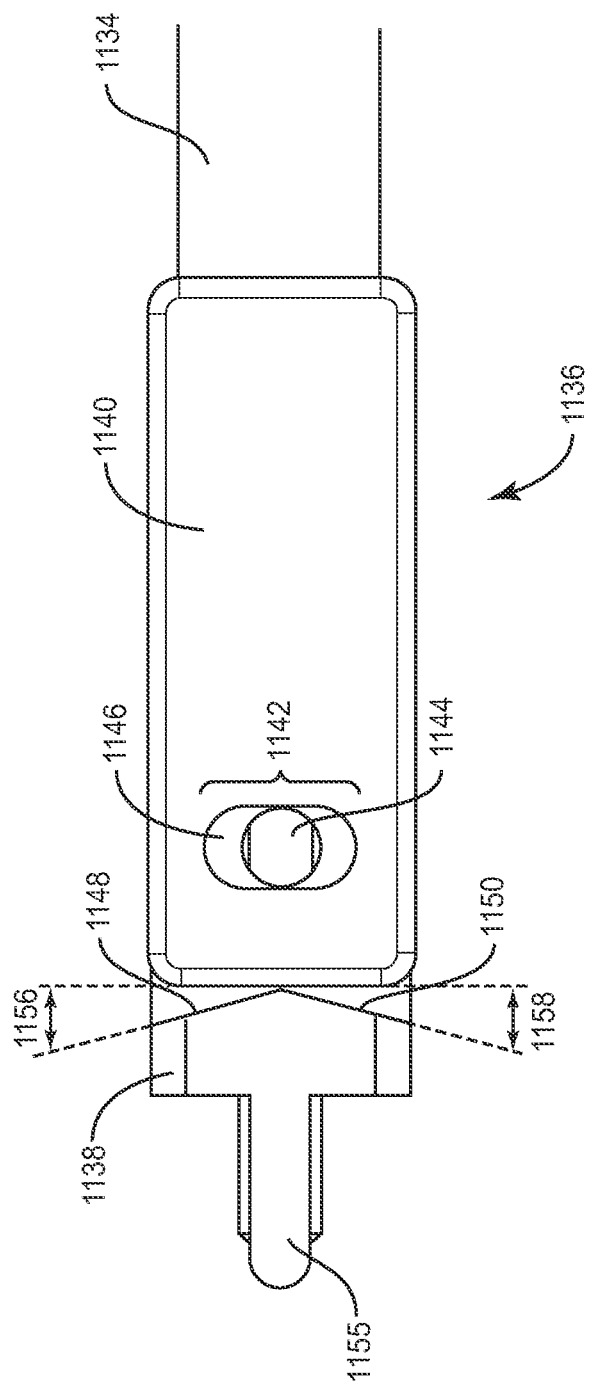
FIG. 28 is a plan view of a portion of the instrument shown in FIG. 26.
Figure 29:
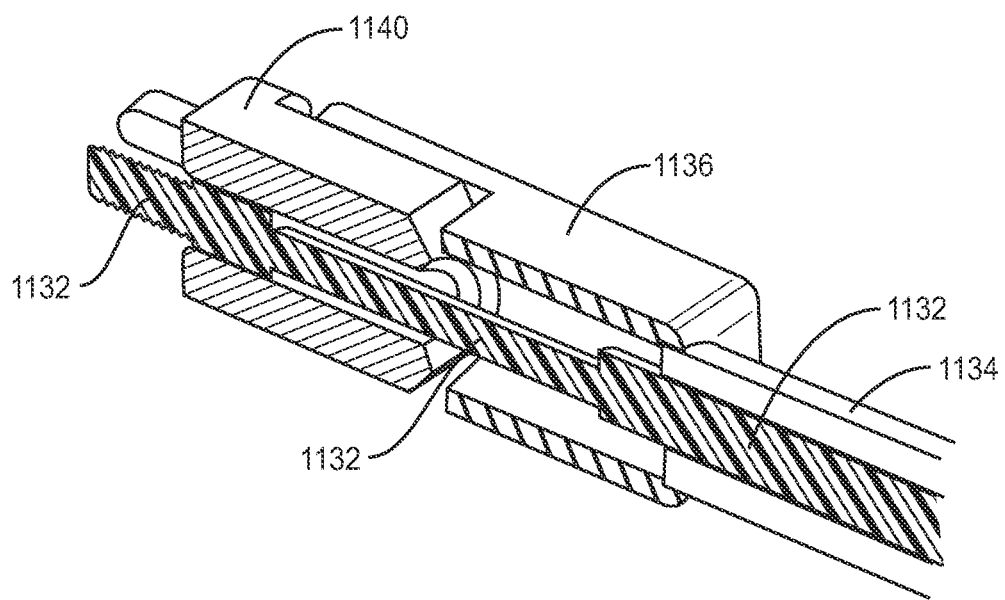
FIG. 29 is a cross-sectional perspective view of the instrument shown in FIG. 26.
Figure 30:
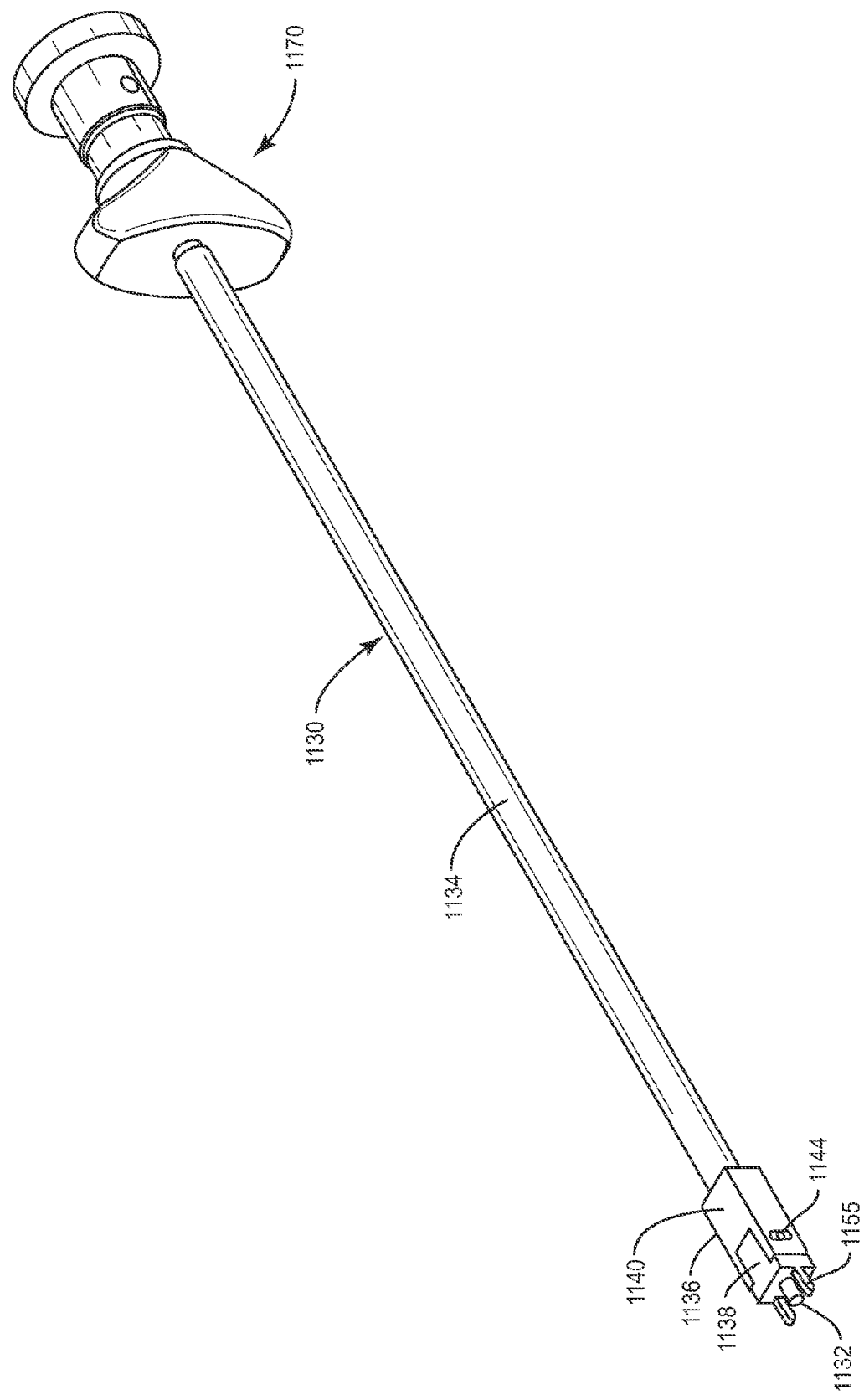
FIG. 30 is a perspective view of the instrument shown in FIG. 26.

In one embodiment, illustrated in FIGS. 26 and 27, the system of the present invention includes an implant 1030, which is similar to implants 30, 230, 430 and 830 having a proximal end 1032, a distal end 1034 opposite proximal end 1032, an upper surface 1040, a lower surface 1042 opposite upper surface 1040, and side surfaces 1044, 1046. Upper and lower surfaces 1040, 1042 are configured to interface with load bearing endplates of adjacent vertebrae, while side surfaces 1044, 1046, proximal end 1032 and distal end 1034 extend between upper and lower surfaces 1040, 1042. Upper and lower surfaces 1040, 1042 include bone engaging features 1052 configured to reduce slipping or movement relative to the vertebrae implant 1030 is placed between.

Implant 1030 has a height defined by the distance between two adjacent vertebrae and a width defined by the distance between proximal end 1032 and distal end 1034. The width of implant 1030 is approximately the width of at least one of the vertebrae implant 1030 is positioned between. Proximal end 1032 includes a proximal face 1036, while distal end 1034 includes a distal face 1038. In one embodiment, proximal face 1036 is planar while distal face 1038 is convexly curved between upper and lower surfaces 1040, 1042 and is configured to allow at least a portion of distal face 1038 to be inserted into a collapsed, undistracted disc space. However, it is envisioned that distal face 1038 may also be pointed, planar or concavely curved between upper and lower surfaces 1040, 1042.

Implant 1030 includes a bore extending longitudinally into proximal end 1032 that extends a distance from proximal end 1032 towards distal end 1034 along the longitudinal axis $a^8$ of implant 1030. The bore is configured to receive a portion of an instrument, such as instrument 130, to engage implant 1030 with the instrument. The bore is disposed equidistant between upper and lower surfaces 1040, 1042, however, it is envisioned that the bore may also be disposed in proximal face 1036 such that the top of bore is closer to upper surface 1040 than the bottom of the bore is from lower surface 1042, or vice versa. The bore has a depth extending longitudinally along longitudinal axis $a^8$ of implant 1030 from proximal face 1036 toward distal face 1038 and terminates before distal face 1038. Implant 1030 further includes channels 1055 extending along side surface 1044 and side surface 1046 a distance from proximal end 1032 towards distal end 1034 along the longitudinal axis $a^8$ of implant 1030. Channels 1055 are each configured to receive locking tabs on an instrument, such as instrument 130. Channels 1055 are disposed equidistant between upper and lower surfaces 1040, 1042, however, it is envisioned that channels 1055 may be disposed in proximal face 1036 such that the top of channels 1055 are closer to upper surface 1040 than the bottom of channels 1055 are from lower surface 1042, or vice versa. A channel 1055 has a depth extending longitudinally along longitudinal axis $a^8$ of implant 1030 from proximal face 1036 toward distal face 1038 and terminates before distal face 1038.

As illustrated in FIGS. 26-30, in addition to implant 1030, the system of the present invention also includes an instrument 1130 configured to engage implant 1030, pivot implant 1030 relative to instrument 1130, lock implant 1030 at a particular angle relative to instrument 1130 and insert implant 1130 at the desired angle. Instrument 1130 includes a first member 1132 and a second member 1134 that is movable relative to first member 1132. Second member 1134 is a sleeve configured to fit about first member 1132 and has an opening in the distal end thereof through which first member 1132 may extend. It is envisioned that first member 1132 and/or second member 1134 may be rectangular, cylindrical or, in the alternative, may have other cross section shapes such as square, hexagonal or octagonal, for example. The distal end of first member 1132 is configured to extend through the bore in proximal end 1032 of implant 1030 to engage instrument 1130 with implant 1030.

Instrument 1130 further includes a pivoting joint 1136 positioned at the distal end of second member 1134 configured to pivot implant 1030 once implant 1030 is engaged with instrument 1130. Pivoting joint 1136 includes a first portion 1138 and a second portion 1140 pivotably connected to first portion 1138 via a pivot point 1142. Pivot point 1142 is defined by a protrusion 1144 on a side surface of first portion 1138 that is received within a corresponding recess 1146 in second portion 1140. When protrusion 1144 is received within recess 1146, first portion 1138 is pivotable relative to second portion 1140 such that first portion 1138 may pivot perpendicularly. First portion 1138 and second portion 1140 each have a rectangular cross section but may have other cross sectional shapes such cylindrical, square or hexagonal, for example. Second portion 1140 has a recess 1152 disposed in the distal end of second portion 1140 configured to receive at least a portion of first portion 1138. As shown in FIG. 26, recess 1142 is rectangular and corresponds to the size and shape of the proximal end of first portion 1138 such that the proximal end of first portion 1138 is received within recess 1142.

First portion 1138 of pivoting joint 1136 includes locking tabs 1155 extending from the distal end of first portion 1138 along side surface 1044 and side surface 1046 of implant 1030 configured to received within channel 1055 on either side of implant 1030. In one embodiment, locking tabs 1155 are disposed closer to the top surface of first portion 1138 than the bottom surface thereof. However it is also envisioned that locking tabs 1155 may be disposed such that locking tabs 1155 are closer to the bottom surface of first portion 1138 than the top surface thereof, or an equal distance form the top and bottom surfaces of first portion 1138. The distance between locking tabs 1155 is approximately equal to the distance between side surfaces 1044, 1046 of implant 1030. More specifically, the distance between locking tabs 1155 is approximately equal to the distance between channel 1055 in side surface 1044 and channel 1055 in side surface 1046. The length of locking tabs 1155 is approximately equal to the depth of channels 1055. Locking tabs 1155 may be formed to at least partially elastically deform to engage implant 1030 such that locking tabs 1155 lock within channels 1055. In particular, locking tabs 1155 may be configured to elastically deform such that locking tabs 1155 may be expanded so that the distance between locking tabs 1155 is greater than the distance between channel 1055 in side surface 1044 and channel 1055 in side surface 1046. Locking tabs 1155 are then positioned over channels 1055, and then return to their original, non-expanded configuration, such that locking tabs 1155 snap into place within channels 1055. When locking tabs 1155 are snapped into place within channels 1055, the distal end of first portion 1138 of pivoting joint 1136 engages proximal face 1036 of implant 1030.

First portion 1138 of pivoting joint 1136 further includes a first lateral face 1148 that forms a first pivoting angle 1156 relative to the planar distal end of second portion 1140 and a second lateral face 1150 that forms a second pivoting angle 1158 relative to the planar distal end of second portion 1140. In one embodiment, first lateral face 1148 and second lateral face 1150 are each disposed at the angle relative to the planar distal end of second portion 1140. It is envisioned that first lateral face 1148 and second lateral face 1150 may each be disposed at a variety of angles (from 0 to 90° and from 0 to −90°) relative to the distal end of second portion 1140 such that first portion 1138 may be pivoted at a variety of angles relative to second portion 1140. First portion 1138 is pivotable relative to second portion 1140 such that first portion 1138 pivots about pivot point 1142. However, the planar distal end of second portion 1140 may engage a portion of first portion 1138 to prevent first portion 1138 from pivoting about pivot point 1142 in at least one direction. For example, first portion 1138 may be pivoted to the first pivoting angle 1156 such that the planar distal end of second portion 1040 engages first lateral face 1148, which prevents first portion 1138 from pivoting upwardly about pivot point 1142. However, first portion 1138 may be pivoted downwardly such that the planar distal end of second portion 1140 engages second lateral face 1150, which prevents first portion 1138 from pivoting downwardly about pivot point 1142.

Pivoting joint 1136 includes a bore extending longitudinally through first and second portions 1138, 1140 configured to create a passage for the distal end of first member 1132 such that the distal end of first member 1132 may extend through the bore in pivoting joint 1136 to engage an implant, such as implant 1030. At least a portion of the distal end of first member 1132 is received within the recess in proximal end 1032. First member 1132 is flexible so as to bend when pivoting joint 1136 is pivoted, while still engaging implant 1030. The recess in proximal end 1032 of implant 1030 has a size and shape which corresponds to that of the distal end of first member 1132 such that the distal end of first member 1132 may be received within the recess in proximal end 1032 to engage implant 1030 and instrument 1130. To engage implant 1030 and instrument 1130, first member 1132 of instrument 1130 is extended through second member 1134 and the bore in pivoting joint 1136 and into the recess in proximal end 1032 of implant 1030.

In operation, implant 1030 is connected to instrument 1130 by first inserting the distal end of first member 1132 into the recess in proximal end 1032, and then positioning locking tabs 1154 into corresponding channels 1054 in implant 1030 until locking tabs 1154 snap into place within channels 1054. First portion 1138 may be pivoted relative to second portion 1140 such that first lateral face 1148 of pivoting joint 1136 engages the distal end of second portion 1140 to maintain first portion 1038 at an angle relative to second portion 1040. Alternatively, first portion 1038 may be pivoted relative to second portion 1140 such that second lateral face 1150 of pivoting joint 1136 engages the distal end of second portion 1140 to maintain first portion 1038 at an angle relative to second portion 1040. Implant 1030 may be inserted between adjacent vertebrae. Implant 1030 may be disconnected from instrument 1130 before of after inserting implant 1030 into an intervertebral space by disengaging the distal end of first portion 1138 from the recess in proximal end 1032 of implant 1030 and removing locking tabs 1154 from channels 1054.

Instrument 1130 may include a handle 1170 having a transverse dimension greater than that of second member 1134 to permit ease of gripping by a surgeon during use. Handle 1170 may be formed of stainless steel, for example, and may have a shape corresponding to that of second member 1134. For example, it is envisioned that the handle 1170 could be cylindrical or, in the alternative, may have other cross section shapes such as square or rectangle, for example. The handle may also have flattened surfaces for receiving hammer blows used to manipulate instrument 1130 to pivot and/or position implant 1030 into the intervertebral disc space.

In one embodiment, the interbody implant system includes an implant having an agent, which includes a bone growth promoting material, which may be disposed, packed or layered within, on or about the components and/or surfaces thereof. The bone growth promoting material, such as, for example, bone graft can be a particulate material, which may include an osteoconductive material such as hydroxyapatite and/or an osteoinductive agent such as a bone morphogenic protein (BMP) to enhance bony fixation of spinal implant 30 with the adjacent vertebrae V.

It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines Spinal implant 30 can be made of radiolucent materials such as polymers. Radiomarkers may be included for identification under x-ray, fluoroscopy, CT or other imaging techniques.

It is envisioned that the agent may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An interbody implant system comprising:
   an implant having an engagement surface and a catch; and
   an instrument extending along a longitudinal axis between opposite proximal and distal ends and including a first member and a second member that is movable relative to the first member, the first member comprising a top portion and a bottom portion that is movable relative to the top portion along the longitudinal axis, the top and bottom portions defining a capture surface configured to capture the catch, the second member including an interface configured to engage the engagement surface to releasably lock the implant in at least one orientation relative to the second member,
   wherein at least one of the engagement surface and the interface include at least one planar face, and
   wherein the second member comprises a first recess having a first spring disposed therein, a second recess that is spaced apart from the first recess having a second spring disposed therein, a notch and an arm that is pivotable relative to a body of the second member, the arm being movable to move the springs between compressed and decompressed states to move the capture surface between an open position to release the implant and a closed position to capture the implant during movement of the implant relative to the second member.

2. The implant system of claim 1, wherein the implant is configured for capture by the first member and rotation relative to the instrument to a plurality of orientations, the implant being releasably lockable by the second member in each of the plurality of orientations.

3. The implant system of claim 1, wherein the at least one planar face includes a proximal face of the implant, the proximal face being disposed in a perpendicular orientation relative to a single straight central longitudinal axis of the implant.

4. The implant system of claim 3, wherein the at least one planar face further includes a first lateral face that converges with the proximal face to form a first angle wherein the implant is pivotable relative to the first member via engagement of the first member with the first angle.

5. The implant system of claim 1, wherein the at least one planar face includes opposing lateral faces of the implant, the lateral faces being disposed in a parallel orientation relative to a single straight central longitudinal axis of the implant.

6. The implant system of claim 1, wherein the at least one planar face includes opposing lateral faces of the implant, the lateral faces being disposed at an angular orientation relative to a single straight central longitudinal axis of the implant.

7. The implant system of claim 1, wherein the at least one planar face includes a distal face of the second member, the distal face being disposed in a perpendicular orientation relative to a longitudinal axis of the instrument, the longitudinal axis being a single straight central longitudinal axis.

8. The implant system of claim 1, wherein the catch includes a pin and the capture surface includes a cavity defined in a distal end of the second member.

9. The implant system of claim 1, wherein the catch includes a pin and the capture surface includes a hook and an elongated gate movable to fix the pin in the hook.

10. The implant system of claim 1, wherein the capture surface is biased to at least one of the open and closed positions.

11. The implant system of claim 1, wherein the implant is configured for capture by the first member and rotation relative to the second member in one direction only.

12. The implant system of claim 1, wherein the longitudinal axis is a single straight central longitudinal axis.

13. The implant system of claim 1, wherein the first spring is disposed in a parallel orientation relative to the longitudinal axis and the second spring is disposed in a perpendicular orientation relative to the longitudinal axis.

14. The implant system of claim 1, wherein a distal end of the arm is removed from the notch, the first spring is decompressed and a proximal end of the arm is disposed within the second recess when the capture surface is in the closed position.

15. The implant system of claim 1, wherein a distal end of the arm is positioned within the notch, the first spring is compressed and a proximal end of the arm is removed from the second recess when the capture surface is in the open position.

16. An interbody implant system comprising:
   an implant having a first end and a second end having an engagement surface including at least one planar face and a catch; and
   an instrument extending along a longitudinal axis between a first end and a second end, the instrument being movable relative to a first member, the first member including a proximal end and a distal end, the first member including a top portion and a bottom portion that is movable relative to the top portion along the longitudinal axis, the top and bottom portions defining a capture surface configured to engage the catch,
   a second member including a proximal end and a distal end, the distal end including a planar interface configured to engage the at least one planar face of the engagement surface to releasably fix the implant relative to the distal end of the second member in one of the plurality of orientations between a first configuration such that the distal end of the second member is movable relative to the implant and a second configuration to capture the catch such that the implant is movable relative to the second member to a plurality of orientations,
   wherein the second member comprises a first recess having a first spring disposed therein, a second recess that is spaced apart from the first recess having a second spring disposed therein, a notch and an arm that is pivotable relative to a body of the second member, the arm being movable to move the springs between compressed and decompressed states to move the capture surface between the first configuration to release the implant and the second configuration to capture the implant during movement of the implant relative to the second member.

17. The implant system of claim 16, wherein the at least one planar face includes opposing lateral faces of the implant, the lateral faces being disposed at an angular orientation relative to a single straight central longitudinal axis of the implant.

18. The implant system of claim 16, wherein the at least one planar face includes a proximal face of the implant disposed in a perpendicular orientation relative to a single straight central longitudinal axis of the implant, and a first lateral face that converges with the proximal face to form a first angle, the implant being pivotable relative to the first member via engagement of the first member with the first angle.

19. An interbody implant system comprising:
a body defining a longitudinal axis extending between a proximal end surface and a distal end surface, said proximal and distal end surfaces extending between opposite top and bottom surfaces, said body comprising opposite first and second planar side surfaces that extend between said proximal and distal surfaces and said top and bottom surfaces, said first and second side planar surfaces extending parallel to one another, said body comprising a proximal end including an inner surface having opposing transverse surfaces, said inner surface defining an inner cavity having a proximal facing opening configured to receive an instrument, said proximal end further including a catch configured for disposal within the inner cavity and disposed in an orientation transverse to said longitudinal axis; and
an instrument extending along a longitudinal axis between opposite proximal and distal ends and including a first member and a second member that is movable relative to the first member, the first member comprising a top portion and a bottom portion that is movable relative to the top portion along the longitudinal axis, the top and bottom portions defining a capture surface configured to capture the catch, the second member including an interface configured to engage the engagement surface to releasably lock the implant in at least one orientation relative to the second member,
wherein at least one of the engagement surface and the interface include at least one planar face, and
wherein the second member comprises a first recess having a first spring disposed therein, a second recess that is spaced apart from the first recess having a second spring disposed therein, a notch and an arm that is pivotable relative to a body of the second member, the arm being movable to move the springs between compressed and decompressed states to move the capture surface between an open position to release the implant and a closed position to capture the implant during movement of the implant relative to the second member.

20. The interbody implant system of claim 19 wherein said proximal end includes opposing lateral faces that extend from opposite sides of said proximal end surface, the lateral faces being disposed at an acute angle relative to a single straight central longitudinal axis of the implant.

21. The interbody implant system of claim 19 wherein said proximal end surface is disposed in a substantially perpendicular orientation relative to a single straight central longitudinal axis of the implant, and a first lateral face that converges with said proximal end surface to form a first acute angle, said implant configured so as to be pivotable relative to said instrument via engagement of said instrument with said first acute angle.

* * * * *

UNITED STATES PATENT AND TRADEMARK OFFICE
CERTIFICATE OF CORRECTION

PATENT NO. : 9,220,607 B2
APPLICATION NO. : 13/283915
DATED : December 29, 2015
INVENTOR(S) : Palmatier et al.

It is certified that error appears in the above-identified patent and that said Letters Patent is hereby corrected as shown below:

Title Page, item (73), under "Assignee", in Column 1, Line 1, delete "Warsaw Oorthopedic, Inc.," and insert -- Warsaw Orthopedic, Inc., --, therefor.

In the Specification

In Column 12, Line 60, delete "form the" and insert -- from the --, therefor.

In Column 18, Line 65, delete "form the" and insert -- from the --, therefor.

In Column 20, Lines 11-12, delete "implant 1130" and insert -- implant 1030 --, therefor.

In Column 20, Line 48, delete "to received" and insert -- to receive --, therefor.

In Column 20, Line 54, delete "form the" and insert -- from the --, therefor.

In Column 22, Line 1, delete "before of" and insert -- before or --, therefor.

In Column 22, Line 24, delete "morphogenic" and insert -- morphogenetic --, therefor.

In Column 22, Line 43, delete "cytokines" and insert. -- cytokines. --, therefor.

Signed and Sealed this
Twenty-sixth Day of April, 2016

Michelle K. Lee
*Director of the United States Patent and Trademark Office*